United States Patent
Young et al.

(10) Patent No.: US 8,566,818 B2
(45) Date of Patent: Oct. 22, 2013

(54) METHOD AND SYSTEM FOR CONFIGURING A CONSOLIDATED SOFTWARE APPLICATION

(75) Inventors: Morris J. Young, Indianapolis, IN (US); Janette Elaine Allen, Indianapolis, IN (US); Schuyler Buck, Muncie, IN (US); Christopher Richard Baker, Fishers, IN (US); Timothy L. Beck, Pendleton, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1186 days.

(21) Appl. No.: 11/999,894

(22) Filed: Dec. 7, 2007

(65) Prior Publication Data

US 2009/0150831 A1    Jun. 11, 2009

(51) Int. Cl.
*G06F 9/445*    (2006.01)

(52) U.S. Cl.
USPC .............. 717/174; 717/168; 717/120; 705/2; 705/3; 715/841

(58) Field of Classification Search
USPC .................. 717/120–121, 168–178; 705/2–3; 715/841
See application file for complete search history.

(56) References Cited

U.S. PATENT DOCUMENTS

| | | | |
|---|---|---|---|
| 5,251,126 A | 10/1993 | Kahn et al. | |
| 5,497,486 A | 3/1996 | Stolfo et al. | |
| 5,671,404 A | 9/1997 | Lizee et al. | |
| 5,671,409 A | 9/1997 | Fatseas et al. | |
| 5,859,966 A * | 1/1999 | Hayman et al. | 726/23 |
| 5,948,064 A * | 9/1999 | Bertram et al. | 709/225 |
| 5,951,300 A | 9/1999 | Brown | |
| 5,995,962 A | 11/1999 | Horowitz | |
| 6,024,699 A | 2/2000 | Surwit et al. | |
| 6,032,119 A | 2/2000 | Brown et al. | |
| 6,322,502 B1 | 11/2001 | Schoenberg et al. | |
| 6,425,863 B1 | 7/2002 | Werner et al. | |
| 6,562,001 B2 | 5/2003 | Lebel et al. | |
| 6,564,105 B2 | 5/2003 | Starkweather et al. | |
| 6,571,128 B2 | 5/2003 | Lebel et al. | |
| 6,577,899 B2 | 6/2003 | Lebel et al. | |
| 6,585,644 B2 | 7/2003 | Lebel et al. | |
| 6,605,038 B1 | 8/2003 | Teller et al. | |
| 6,635,014 B2 | 10/2003 | Starkweather et al. | |

(Continued)

FOREIGN PATENT DOCUMENTS

| | | |
|---|---|---|
| DE | 20217855 | 2/2003 |
| EP | 0970655 | 1/2000 |

(Continued)

OTHER PUBLICATIONS

Wang, C. et al.; *"A Corba-Based Object Framework with Patient Identification Translation and Dynamic Linking, Methods for Exchanging Patient Data,"* Methods of Information in Medicine, Mar. 1999, pp. 56-65, vol. 38, No. 1, F.K.Schattauer Verlagsgesellschaft mbH, Germany.

(Continued)

*Primary Examiner* — Lewis A Bullock, Jr.
*Assistant Examiner* — Tina Huynh
(74) *Attorney, Agent, or Firm* — Faegre Baker Daniels LLP

(57) ABSTRACT

A system and method for selectively configuring features and functions of a consolidated software application for particular end users.

33 Claims, 20 Drawing Sheets

(56) References Cited

U.S. PATENT DOCUMENTS

| | | | |
|---|---|---|---|
| 6,648,821 B2 | 11/2003 | Lebel et al. | |
| 6,659,948 B2 | 12/2003 | Lebel et al. | |
| 6,668,196 B1 | 12/2003 | Villegas et al. | |
| 6,684,191 B1 | 1/2004 | Barnard et al. | |
| 6,687,546 B2 | 2/2004 | Lebel et al. | |
| 6,694,191 B2 | 2/2004 | Starkweather et al. | |
| 6,715,144 B2* | 3/2004 | Daynes et al. | 717/174 |
| 6,733,446 B2 | 5/2004 | Lebel et al. | |
| 6,740,075 B2 | 5/2004 | Lebel et al. | |
| 6,748,402 B1 | 6/2004 | Reeves | |
| 6,758,810 B2 | 7/2004 | Lebel et al. | |
| 6,781,522 B2 | 8/2004 | Sleva et al. | |
| 6,804,656 B1 | 10/2004 | Rosenfeld et al. | |
| 6,810,290 B2 | 10/2004 | Lebel et al. | |
| 6,811,533 B2 | 11/2004 | Lebel et al. | |
| 6,811,534 B2 | 11/2004 | Bowman, IV et al. | |
| 6,813,519 B2 | 11/2004 | Lebel et al. | |
| 6,852,104 B2 | 2/2005 | Blomquist | |
| 6,873,268 B2 | 3/2005 | Lebel et al. | |
| 6,873,807 B2 | 3/2005 | Umetsu | |
| 6,958,705 B2 | 10/2005 | Lebel et al. | |
| 6,990,434 B2 | 1/2006 | Minogue et al. | |
| 7,020,508 B2 | 3/2006 | Stivoric et al. | |
| 7,024,236 B2 | 4/2006 | Ford et al. | |
| 7,029,455 B2 | 4/2006 | Flaherty | |
| 7,041,468 B2 | 5/2006 | Drucker et al. | |
| 7,050,735 B2 | 5/2006 | Bardolatzy et al. | |
| 7,063,665 B2 | 6/2006 | Hasegawa et al. | |
| 7,069,581 B2 | 6/2006 | Fu et al. | |
| 7,082,334 B2 | 7/2006 | Boute et al. | |
| 7,113,946 B2 | 9/2006 | Cosic | |
| 7,120,488 B2 | 10/2006 | Nova et al. | |
| 7,165,062 B2 | 1/2007 | O'Rourke | |
| 7,179,226 B2 | 2/2007 | Crothall et al. | |
| 7,181,350 B2 | 2/2007 | Oberding et al. | |
| 7,203,937 B1* | 4/2007 | Kyle et al. | 717/168 |
| 7,206,824 B2* | 4/2007 | Somashekar et al. | 709/220 |
| 7,207,009 B1 | 4/2007 | Aamodt et al. | |
| 7,228,541 B2* | 6/2007 | Gupton et al. | 717/175 |
| 7,395,513 B2* | 7/2008 | Zimniewicz et al. | 715/841 |
| 7,587,715 B1* | 9/2009 | Barrett et al. | 717/176 |
| 7,676,387 B2* | 3/2010 | Childress et al. | 705/4 |
| 7,693,731 B1* | 4/2010 | Weber et al. | 705/4 |
| 2002/0016568 A1 | 2/2002 | Lebel et al. | |
| 2002/0029776 A1 | 3/2002 | Blomquist | |
| 2002/0040208 A1 | 4/2002 | Flaherty et al. | |
| 2002/0059299 A1 | 5/2002 | Spaey | |
| 2002/0082665 A1* | 6/2002 | Haller et al. | 607/60 |
| 2002/0116477 A1* | 8/2002 | Somashekar et al. | 709/220 |
| 2002/0140976 A1 | 10/2002 | Borg et al. | |
| 2002/0193679 A1 | 12/2002 | Malave et al. | |
| 2003/0002848 A1 | 1/2003 | Kawaoka et al. | |
| 2003/0011646 A1 | 1/2003 | Levine et al. | |
| 2003/0065308 A1 | 4/2003 | Lebel et al. | |
| 2003/0065536 A1 | 4/2003 | Hansen et al. | |
| 2003/0069758 A1 | 4/2003 | Anderson et al. | |
| 2003/0098869 A1 | 5/2003 | Arnold et al. | |
| 2003/0140044 A1 | 7/2003 | Mok et al. | |
| 2003/0145206 A1 | 7/2003 | Wolosewicz et al. | |
| 2003/0163088 A1 | 8/2003 | Blomquist | |
| 2003/0199739 A1 | 10/2003 | Gordon et al. | |
| 2003/0208465 A1 | 11/2003 | Yurko et al. | |
| 2004/0030987 A1 | 2/2004 | Manelli | |
| 2004/0038389 A1 | 2/2004 | Maus et al. | |
| 2004/0073464 A1 | 4/2004 | Huang | |
| 2004/0086314 A1 | 5/2004 | Chen et al. | |
| 2004/0111296 A1 | 6/2004 | Rosenfeld et al. | |
| 2004/0119742 A1 | 6/2004 | Silbey et al. | |
| 2004/0172284 A1 | 9/2004 | Sullivan et al. | |
| 2005/0004947 A1 | 1/2005 | Emlet et al. | |
| 2005/0010452 A1 | 1/2005 | Lusen | |
| 2005/0102667 A1* | 5/2005 | Barta et al. | 717/174 |
| 2005/0137653 A1 | 6/2005 | Friedman et al. | |
| 2005/0159977 A1 | 7/2005 | Green et al. | |
| 2005/0182655 A1 | 8/2005 | Merzlak et al. | |
| 2005/0187794 A1 | 8/2005 | Kimak | |
| 2005/0192844 A1 | 9/2005 | Esler et al. | |
| 2005/0246343 A1* | 11/2005 | Burns et al. | 707/10 |
| 2005/0259945 A1 | 11/2005 | Splaver | |
| 2006/0010014 A1 | 1/2006 | Brown | |
| 2006/0015867 A1* | 1/2006 | Drittler et al. | 717/174 |
| 2006/0020491 A1 | 1/2006 | Mongeon et al. | |
| 2006/0031094 A1 | 2/2006 | Cohen et al. | |
| 2006/0095298 A1 | 5/2006 | Bina | |
| 2006/0123414 A1* | 6/2006 | Fors et al. | 717/177 |
| 2006/0136872 A1* | 6/2006 | Barr et al. | 717/114 |
| 2006/0136906 A1* | 6/2006 | Hughes et al. | 717/174 |
| 2006/0155581 A1 | 7/2006 | Eisenberger et al. | |
| 2006/0161460 A1 | 7/2006 | Smitherman et al. | |
| 2006/0167367 A1 | 7/2006 | Stanczak et al. | |
| 2006/0178910 A1 | 8/2006 | Eisenberger et al. | |
| 2006/0184524 A1 | 8/2006 | Pollanz | |
| 2006/0224638 A1 | 10/2006 | Wald et al. | |
| 2006/0272652 A1 | 12/2006 | Stocker et al. | |
| 2007/0027506 A1* | 2/2007 | Stender et al. | 607/60 |
| 2007/0033074 A1 | 2/2007 | Nitzan et al. | |
| 2007/0048691 A1 | 3/2007 | Brown | |
| 2007/0055940 A1 | 3/2007 | Moore et al. | |
| 2007/0088525 A1 | 4/2007 | Fotiades et al. | |
| 2007/0089071 A1 | 4/2007 | Zinn et al. | |
| 2007/0130073 A1* | 6/2007 | Celli et al. | 705/51 |
| 2007/0179352 A1 | 8/2007 | Randlov et al. | |
| 2007/0179975 A1 | 8/2007 | Teh et al. | |
| 2007/0185390 A1 | 8/2007 | Perkins et al. | |
| 2007/0189590 A1 | 8/2007 | Fidrich et al. | |
| 2007/0219432 A1 | 9/2007 | Thompson | |
| 2007/0232866 A1 | 10/2007 | Nephin et al. | |
| 2007/0276197 A1 | 11/2007 | Harmon | |

FOREIGN PATENT DOCUMENTS

| | | |
|---|---|---|
| EP | 0649316 | 12/2000 |
| EP | 1194864 | 4/2002 |
| EP | 1416417 | 5/2004 |
| EP | 1647929 | 4/2006 |
| EP | 1662417 | 5/2006 |
| EP | 1684 172 | 7/2006 |
| JP | 04/145774 | 5/2004 |
| JP | 04/145775 | 5/2004 |
| JP | 04/145776 | 5/2004 |
| JP | 07/058685 | 3/2007 |
| WO | WO9609590 | 3/1996 |
| WO | WO0018449 | 4/2000 |
| WO | WO0065522 | 11/2000 |
| WO | WO0072181 | 11/2000 |
| WO | WO0174229 | 10/2001 |
| WO | WO0200111 | 1/2002 |
| WO | WO02078512 | 10/2002 |
| WO | WO03015838 | 2/2003 |
| WO | WO2005037095 | 4/2005 |
| WO | WO2005096206 | 10/2005 |
| WO | WO2006050485 | 5/2006 |
| WO | WO2007005530 | 1/2007 |
| WO | WO2007084502 | 7/2007 |
| WO | WO2007093482 | 8/2007 |

OTHER PUBLICATIONS

Bilenko, M. et al.; "*Adaptive Name Matching in Information Integration*," IEEE Intelligent Systems; Sep. 2003, vol. 18, No. 5; p. 16-23, IEEE Computer Society.

Frenger, Paul; "*GRANNIE 2: a Ubiquitious, Protean Robotic Guardian Angel*," Automation Science and Engineering, Sep. 1, 2007, pp. 857-862, IEEE International Conference on IEEE.

Frenger, Paul; "*GRANNIE: A Scalable, Interactive, Artificial Intelligence Supervisory System for Medical Devices*," Proceedings of Can. Med. Bio. Engr. Conference, 2007, p. 256-259.

"CoPilot Health Management System Version 3.1," User's Guide, Mar. 2007, 230 pp., ART 10641 Rev. D, Abbott Diabetes Care, Inc.

"MediSense® Precision Link® Diabetes Data Management Software," User's Guide, May 2006, 58 pp., 116-412 Rev. AC, Abbott Diabetes Care, Inc.

(56) References Cited

OTHER PUBLICATIONS

Albisser, Michael A.; "A Graphical User Interface for Diabetes Management Than Integrates Glucose Prediction and Decision Support," Diabetes Technology & Therapeutics, 2005, pp. 264-273, vol. 7, No. 2.

Janssen et al., "Acensia® Winglucofacts® Professional Intelligent Diabetes Management Software Is an Effective Tool for the Management of Diabetes," Bayer HealthCare Clinical Summary Report, Jul. 2005, 10 pp.

Joshy et al.; "Diabetes Information Systems: A Rapidly Emerging Support for Diabetes Surveillance and Care," Diabetes Technology & Therapeutics, 2006, pp. 587-597, vol. 8, No. 5.

"OneTouch Diabetes Management Software," User Manual, 2006, 173 pp., v. 2.3.1, Lifescan, Inc.

"Getting Started, CareLink Personal Therapy Management Software for Diabetes," Brochure, 2007, 20 pp., Medtronic Minimed, Inc.

"Accu-Chek® Camit Pro Diabetes Management Software," User's Manual, 2005, 220 pp., v.2.1 and Addendum v. 2,4, Roche Diagnostics Corp.

"Accu-Chek® Compass Diabetes Care Software," User's Guide, 2005, 74 pp., Roche Diagnostics Corp.

"Accu-Chek® Diabetes Assistant," accessed with notional data and printed from www.diabetesassistant.com on Jan. 16, 2007, 20 pp., Roche Diagnostics Corp.

International Report and Written Opinion for PCT/US2008/009860 issued by the European Patent Office on Apr. 16, 2009 (14 pgs.).

* cited by examiner

METHOD AND SYSTEM FOR CONFIGURING A CONSOLIDATED SOFTWARE APPLICATION

BACKGROUND AND SUMMARY OF THE INVENTION

The present invention relates a method and system for selectively configuring features and functions of a consolidated software application for particular end users. More particularly, the present invention permits multiple levels of customization of a consolidated software application by marketing groups, system administrators, and end users.

One particular consolidated software application in an illustrated embodiment relates to a healthcare management system consolidated software application. Many fields of medical treatment and healthcare require monitoring of certain body functions, physical states and conditions, and patient behaviors. Thus, e.g., for patients suffering from diabetes, a regular check of the blood glucose level forms an essential part of the daily routine. The blood glucose level has to be determined quickly and reliably, often several times per day. Medical devices are used to facilitate the collection of medical information without unduly disturbing the lifestyle of the patient. A large number of medical devices for monitoring various body functions are commercially available. Also, medical treatment and healthcare may require monitoring of exercise, diet, meal times, stress, work schedules and other activities and behaviors.

To reduce the frequency of necessary visits to doctors, the idea of home care gained popularity over the recent years. Technological advancements in medicine led to the increased use of medical devices. Many of these medical devices, such as meters and medicine delivery devices, are able to collect and store measurements and other data for long periods of time. Other devices, such as computers, portable digital assistants (PDAs), and cell phones, have been adapted to medical uses by the development of software directed to the collection of healthcare data. These advancements led to the development of health management systems that enable collection and use of large numbers of variables and large amounts of healthcare data.

A common feature of health management systems is the ability to convey information. Information can include raw data, graphical representations of data such as statistical display objects, explanations and textual interpretations, inferential information and so on. Communication and understanding can be improved by using interactive graphs and reports to convey information. Interactivity is achieved using computing devices and software applications. Generally described, individuals can interact with software applications residing on computing devices, such as personal computers, hand-held computers, mobile computing devices, and the like in a variety of ways. In one particular embodiment, the development of graphical user interfaces (GUI) facilitates user interaction with these various software applications resident in the computing device. For example, a user may manipulate a graphical user interface to interact with a data processing application or to communicate with other computing devices and/or users via a communication network.

In a typical embodiment, a GUI can display a number of display objects that are individually manipulable by a user utilizing a user input device. For example, the user can utilize a computer keyboard, mouse, touch screen, touch pad, roller ball or voice commands and the like to select a particular display object and to further initiate an action corresponding to the selected display object. While user input devices have been described in the context of devices configured to manipulate display objects and provide commands to the computing device, generally speaking a user input device is any device capable of providing user input to a computing device and input is not limited to the provision of commands. User input may additionally comprise data which may be provided by medical devices, or computing devices including PDAs and phones.

A consolidated software application illustratively includes software having a plurality of different features to perform the variety of functions as discussed herein. However, some features and functions contained in the consolidated software application may not be useful to particular groups of users. For example, patients or consumers do not need all the same feature sets and functions that a healthcare professional, managed care provider, health maintenance organization (HMO) or insurance company representative may need. Therefore, it is desirable that the consolidated software application be customizable to selectively display certain features and functions on the GUI accessible by the end user. As discussed in detail herein, users in certain geographic regions may also prefer different features and functions. In addition, user with rights in certain fields of use may be authorized to access only certain features and functions. The system of the present invention permits multiple levels of customization of the consolidated software application to address these varying needs.

In an illustrated embodiment of the present invention, a method is provided for customizing a consolidated software application including a plurality of features and functions for a particular end user. The method comprises activating selected features and functions of the consolidated software application during installation of the consolidated software application on a computing device having a user interface accessible by an end user, displaying activated features and functions which were activated during the activating step on a user interface accessible by a system administrator, permitting the system administrator to selectively enable and disable activated features and functions after installation of the consolidated software application on the computing device, displaying activated and enabled features and functions on the user interface accessible to the end user, permitting the end user to selectively show and hide active and enabled features and functions from display on the user interface, and removing those features and functions that the end user selects to hide from display of the user interface accessible to the end user.

In one illustrated embodiment, information related to non-active features and functions of the consolidated software application which were not activated during the activating step is not displayed on the user interfaces accessible by the system administrator and the end user. In addition, information related to disabled features and functions that were disabled by the system administrator during the selectively enabling and disabling activated features step is also not displayed on the user interface accessible by the end user.

In another illustrated embodiment of the present invention, a method of multi-level customization of a consolidated software application by a marketing group, a system administrator, and an end user is provided. The method comprises permitting a marketing group to selectively activate the features and functions of the consolidated software application based on at least one of a geographic region of the end user, a type of end user, and a permitted field of use for the end user during installation of the consolidated software application on a computing device having a user interface accessible by the end user, permitting a system administrator to selectively enable and disable activated features after installation of the consolidated software application, permitting the end user to selectively show and hide active and enabled features and functions from display on the user interface, and removing those features and functions that the end user selects to hide from a display of the user interface accessible to the end user.

In one illustrated embodiment, the consolidated software application is configured to provide a plurality of different features and functions to process physiological information data received from a portable device related to management of a health condition. The consolidated software application also includes instructions to display representations of physiological information data on the user interface. Illustratively, the consolidated software application includes a plurality of styles of display icons, graphics, backgrounds and color schemes which may be used on a display of the user interface accessible by the end user. The marketing group activates selected styles of icons, graphics, backgrounds and color schemes to adjust a look and feel of the software.

In yet another illustrated embodiment of the present invention, a healthcare management system is configured to receive and process physiological information data related to at least one patient from a portable device. The healthcare management system comprises a computing device configured to access and download physiological information data from a portable device, a memory accessible by the computing device to store the downloaded physiological information data, at least one user interface having a display which receives display information from computing device, and software configured to operate on the computing device and implement a plurality of different features and functions to manage the physiological information data from the portable device related to management of a health condition. The software includes instructions to display representations of physiological information data included in the memory on the display of the user interface. The system also comprises means for activating selected features and functions of the consolidated software application during installation of the consolidated software application on the computing device, means for displaying activated features and functions which were activated by the activating means on the display of the user interface accessible by a system administrator, means for permitting the system administrator to selectively enable and disable activated features and functions after installation of the consolidated software application on the computing device, means for displaying activated and enabled features and functions on the user interface accessible to the end user, means for permitting the end user to selectively show and hide active and enabled features and functions from display on the user interface, and means for displaying information related to those features and functions that the end user selects to show on the display on the user interface accessible to the end user.

Additional features and advantages of the present invention will become apparent to those skilled in the art upon consideration of the following detailed description of illustrative embodiments exemplifying the best mode of carrying out the invention as presently perceived.

BRIEF DESCRIPTION OF THE DRAWINGS

The foregoing aspects of this invention will become more readily appreciated as the same become better understood by reference to the following detailed description when taken in conjunction with the accompanying drawings.

Figure 1:
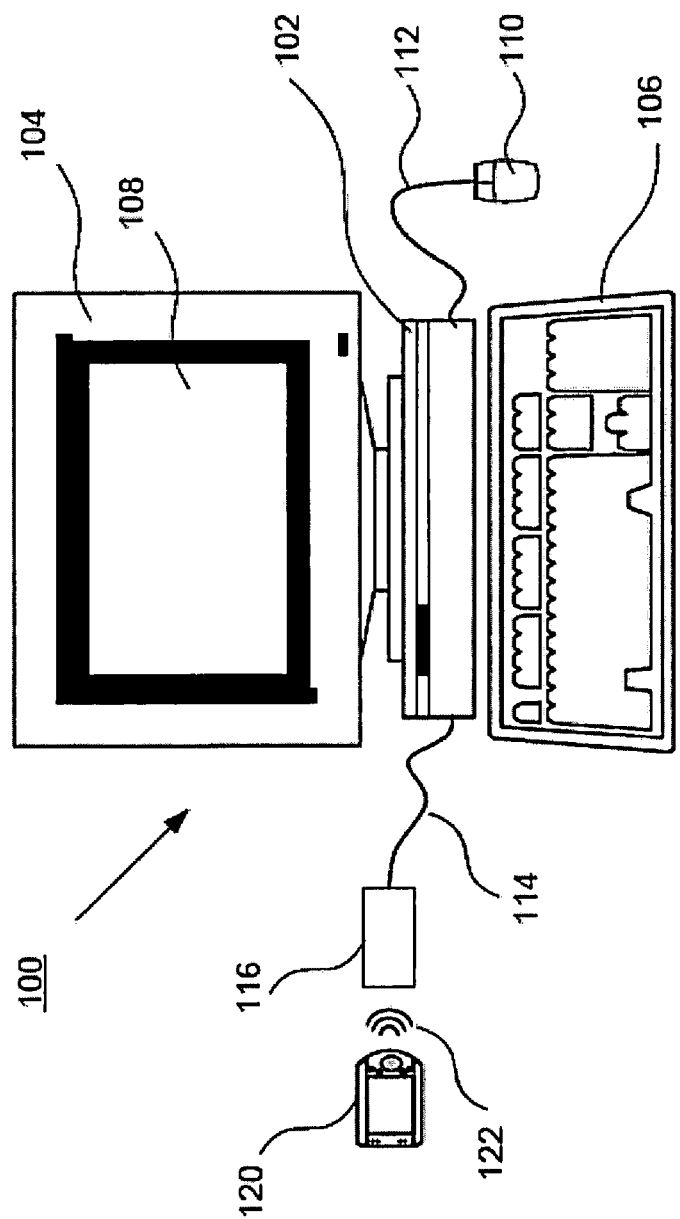
FIG. 1 is a block diagram of a system according to the invention comprising a computing device configured to access a medical device.

Corresponding reference characters indicate corresponding parts throughout the several views. Although the drawings represent embodiments of various features and components according to the present invention, the drawings are not necessarily to scale and certain features may be exaggerated in order to better illustrate and explain the present invention. The exemplification set out herein illustrates embodiments of the invention, and such exemplifications are not to be construed as limiting the scope of the invention in any manner.

DETAILED DESCRIPTION OF THE DRAWINGS

For the purposes of promoting an understanding of the principles of the invention, reference will now be made to the embodiments illustrated in the drawings, which are described below. The embodiments disclosed below are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended. The invention includes any alterations and further modifications in the illustrated devices and described methods and further applications of the principles of the invention which would normally occur to one skilled in the art to which the invention relates.

The detailed descriptions which follow are presented in part in terms of algorithms and generic representations of operations on data bits within a computer memory representing alphanumeric characters or other information. These descriptions and representations are the means used by those skilled in the data processing arts to most effectively convey the substance of their work to others skilled in the art.

An algorithm is here, and generally, conceived to be a sequence of steps leading to a desired result. These steps are those requiring physical manipulations of physical quantities. Usually, though not necessarily, these quantities take the form of electrical or magnetic signals capable of being stored, transferred, combined, compared, and otherwise manipulated. It proves convenient at times, principally for reasons of common usage, to refer to these signals as bits, values, markers, characters, display data, terms, numbers, or the like. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory, rather they represent specific electronic structural elements which impart a physical organization on the information stored in memory. More than mere abstraction, the data structures are specific electrical or magnetic structural elements in memory which simultaneously represent complex data accurately and may provide increased efficiency in computer operation.

Further, the manipulations performed are often referred to in terms, such as comparing or selecting, commonly associated with mental operations performed by a human operator. No such capability of a human operator is necessary in the operations described herein which form part of the present invention. The operations are typically machine operations. Useful machines for performing the operations of the present invention include general purpose digital computers or other similar devices. In all cases the distinction between the method operations in operating a computer and the method of computation itself should be recognized. The present invention relates to a method and apparatus for operating a computer in processing electrical or other (e.g., mechanical, chemical) physical signals to generate other desired physical signals.

The present invention also relates to an apparatus for performing these operations. This apparatus may be specifically constructed for the required purposes or it may comprise a general purpose computer as selectively activated or reconfigured by a computer software application stored in the computer. The algorithms presented herein are not inherently related to any particular computer or other apparatus. In particular, various general purpose machines may be used with software applications written in accordance with the teachings herein, or it may prove more convenient to construct more specialized apparatus to perform the required method steps. The required structure for a variety of these machines will appear from the description below. Although the following description details operations in terms of a graphic user interface using display objects, the present invention may be practiced with text based interfaces, or even with voice or optically activated interfaces.

Turning now to the drawings, FIG. 1 depicts an exemplary embodiment of a system according to the invention for managing data. A particular embodiment of the system is the ACCU-CHEK® 360° diabetes management system distributed by Roche Diagnostics Corporation. The system receives data from a plurality of sources, allows users to modify data, and displays data in a plurality of formats and devices. To improve communication and understanding, the system allows marketing groups, system administrators and end users to choose when and how to display information. Marketing groups, system administrators and end users can choose from a plurality of graph formats, and can also choose how to graph data. Users can combine graphs, tables, and comments on the same screen display and can view the screen display on a computer screen or can print it.

Referring to FIG. 1, a computing device 100 is shown. Computing device 100 may be a general purpose computer or a portable computing device. Although computing device 100 is illustrated as a single computing device, it should be understood that multiple computing devices may be used together, such as over a network or other methods of transferring data. Exemplary computing devices include desktop computers, laptop computers, personal data assistants ("PDA"), such as BLACKBERRY brand devices, cellular devices, tablet computers, infusion pumps, blood glucose meters, or an integrated device including a glucose measurement engine and a PDA or cell phone. In other words, the application 130 may be run on a device such as a meter, pump, or other integrated device instead of a personal computer or network server.

Computing device 100 has access to a memory. The memory is a computer readable medium and may be a single storage device or multiple storage devices, located either locally with computing device 100 or accessible across a network. Computer-readable media may be any available media that can be accessed by a computer 102 and includes both volatile and non-volatile media. Further, computer readable-media may be one or both of removable and non-removable media. By way of example, and not limitation, computer-readable media may comprise computer storage media. Exemplary computer storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store the desired information and which can be accessed by the computing device 100.

The memory illustratively includes one or more patient databases and data management software system. Patient databases include physiological information related to one or more patients. Exemplary physiological information includes blood glucose values, A1c values, Albumin values, Albumin excretion values, body mass index values, blood pressure values, carbohydrate values, cholesterol values (total, HDL, LDL, ratio) creatinine values, fructosamine values, HbA1 values, height values, insulin dose values, insulin rate values, total daily insulin values, ketone values, microalbumin values, proteinuria values, heart rate values, temperature values, triglyceride values, and weight values. Physiological information may be provided directly by the patient, provided by a caregiver, and/or provided by one or more sensors or remote devices 120 discussed below. Exemplary sensors are provided in insulin pumps and glucose meters. The physiological information is related to time information which corresponds to the time the measurement was taken or represents a period of time within which a measurement was taken.

Healthcare management software system includes instructions on a consolidated software application 130 which when executed by computing device 100 present physiological information or information based on physiological information to an output device such as display 104. Exemplary information presented by healthcare management software system to output device 104 include reports and graphs such as, for example, diaries of blood glucose values and reports showing a plurality of blood glucose values and the times or times blocks to which the blood glucose values correspond. Exemplary reports also include standard day reports wherein the blood glucose values are grouped according to the time of day taken, standard week reports wherein the blood glucose values are grouped according to the day of the week taken, trend graphs to illustrate temporal trends in blood glucose values, and other suitable reports and/or graphs.

Computing device 100 typically has access to output devices. Exemplary output devices include fax machines, displays, printers, e-mail, instant messaging devices and files. Files may have various formats. In one embodiment, files are portable document format (PDF) files. In one embodiment, files are formatted for display by an Internet browser, such as Internet Explorer available from Microsoft of Redmond, Wash., and may include one or more of HyperText Markup Language ("HTML"), or other formatting instructions. In one embodiment, files are files stored in memory for transmission to another computing device and eventual presentation by another output device or to at least influence information provided by the another output device.

In one embodiment, healthcare management software system is a diabetes care software which is loaded on a computing device 100. The diabetes care software interacts with a blood glucose meter 120 to receive blood glucose values and other physiological information. The diabetes care software system then is able to present the blood glucose values to the patient, caregiver or payor for review. Computing device 100 is illustratively a personal computer 102. Computing device 100 is coupled to an output device 104, illustratively a display screen 108. Computing device 100 is further coupled to a plurality of input devices. A first exemplary input device is a keyboard 106. A second exemplary input device is a mouse 110 connected to computer 102 by a cable 112. A third exemplary input device is a modulated signal transceiver 116, in electronic communication with computer 102 through a cable 114. Transceiver 116 is configured to transmit and receive a modulated signal 122 and to establish communications to and from a remote portable device 120. An exemplary remote portable device 120 is a blood glucose meter. Another exemplary remote device is an infusion pump.

In one embodiment, blood glucose meter 120 is assigned to a patient and associated with that patient in the healthcare management software system. Thus, when physiological information from blood glucose meter 120 is transferred to healthcare management software system, the physiological information from blood glucose meter 120 automatically populates database records in patient database relating to that patient along with the time information related to the physiological information. In one embodiment, meter 120 provides blood glucose values and test times corresponding to the blood glucose values. The test times including both day and time information.

Although a blood glucose meter 120 is shown, any medical device may be implemented having data to be used by healthcare management software system. Medical devices are devices capable of recording patient data and transferring data to software applications and may include monitors which record values of measurements relating to a patient's state and information such as the time and date when the measurement was recorded. Medical devices may also be devices configured to provide medications to patients such as, for example, insulin pumps. These devices, generally, record dosage amounts as well as the time and date when the medication was provided. A medical device may also comprise a computing device integraded or coupled with a device for recording medical data including without limitation a computer, a personal digital assistant (PDA), a phone, or a BlackBerry device. Furthermore, the system 100 may be integrated with the medical device 120 thereby eliminating the necessity of generating and transmitting a modulated signal.

Computing device 100 may be used by the patient, a caregiver, insurance provider, managed care provider, health maintenance organization (HMO) or anyone having or using relevant data pertaining to a patient. Computing device 100 may be located in a patient's home, a healthcare facility, a drugstore, a kiosk, or any other convenient place. In an alternative embodiment, computing device 100 may be connected to a remote computing device, such as at a caregiver's facility or a location accessible by a caregiver, and physiological information in patient database, or the complete patient database, may be transferred between them. In this embodiment, computing device 100 and the remote device are configured to transfer physiological information and/or time information in patient database, or the complete patient database, between them through a data connection such as, for example, via the Internet, cellular communications, or the physical transfer of a memory device such as a diskette, USB key, compact disc, or other portable memory device. Computing device 100 and/or the remote portable device 120, may be configured to receive physiological information from a medical device or, alternatively, to receive physiological information transferred from the other of computing device and the remote device.

The drives and their associated computer storage media discussed above provide storage of computer-readable instructions, software applications, data structures, program modules and other data for the computing device 100. A user may enter commands and data into the computing device 100 through a user input device such as a keyboard 106 and/or a mouse 110 or any other user input device. Other user input devices (not shown) may include a microphone, a touch screen, a joystick, a game pad, a satellite dish, a scanner, or the like. These and other input devices are often connected to the processing unit through a user input interface and may be connected by other interface and bus structures, such as a parallel port, game port or a universal serial bus (USB).

The system comprises one or more software applications included in a consolidated software application 130 discussed below, configured to receive, organize, and use data. Data may have various sources. The consolidated software application 130 is configured to upload data, to merge data from other origin databases, and to enable users to manually add and modify data.

The system is configured to display information in a plurality of forms and formats. While the screen display has been explained in detail with reference to a display device comprising a video screen for convenience, the term display device is not intended to be so limiting. The term display device includes any device capable of displaying bitmap images or mapped images of any kind. Thus, information may be shown by projecting a screen display onto a video screen, projecting it from a video projector, or by printing the screen display on a printer. The screen display may also be communicated via e-mail or fax.

Figure 2:
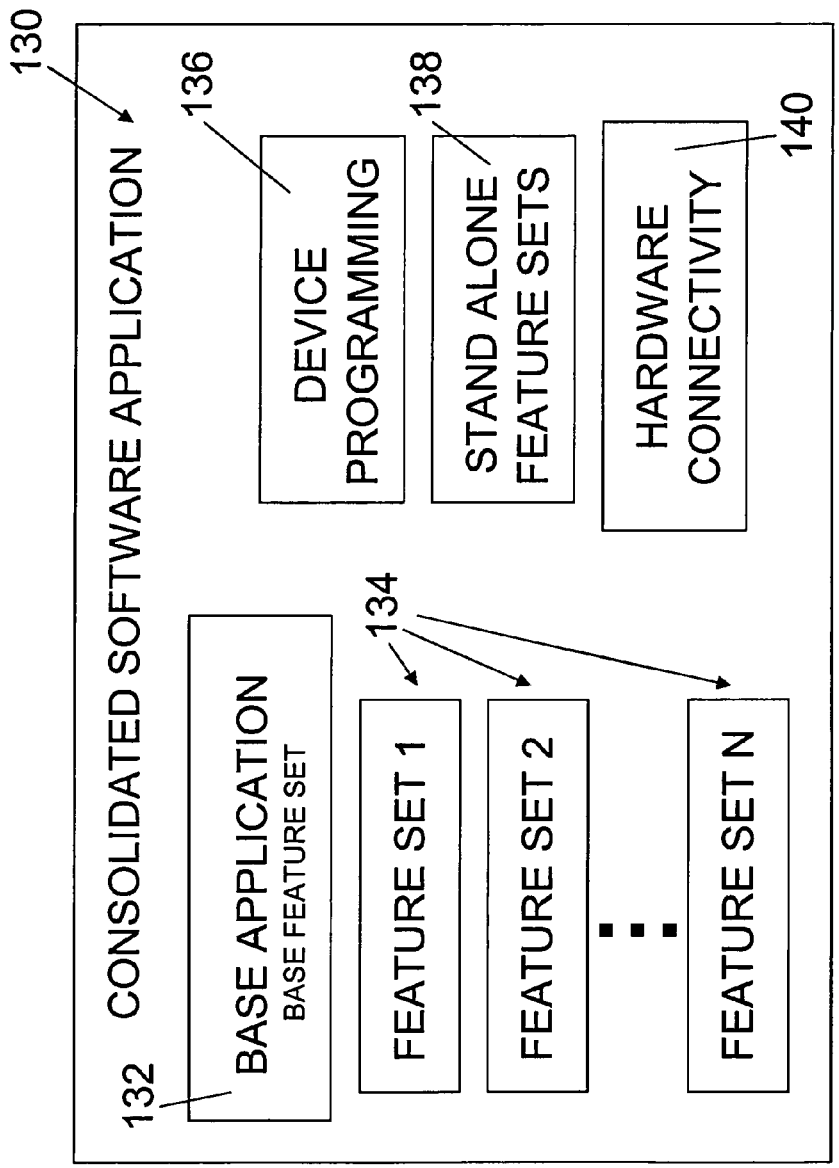
FIG. 2 is a block diagram illustrating a consolidated software application of the present invention.

FIG. 2 illustrates a consolidated software application in accordance with the present invention. The consolidated software application 130 includes a base application 132. The base application 132 includes a base feature set which is illustratively a minimum set of features and functions that are operable when the consolidated software application 130 is executed by an end user. The consolidated software application 130 further includes a plurality of additional feature sets 134, illustrated as feature sets 1, 2 . . . N in FIG. 2, which are dependent on the base application 132. These additional feature sets 134, while included in the consolidated software application 130, are not part of the base application 132. In other words, feature sets 134 are dependent on and related to the base application 132, but are not part of the base feature set of base application 132.

The consolidated software application 130 may also include additional software such as device programming software 136. Device programming software 136 may be used to program or add functionality to certain devices, such as, for example, blood glucose meters, insulin pumps, or other medical devices related to physiological information as discussed above.

Consolidated software application 130 may also include stand alone feature sets 138. These stand alone feature sets 138 are typically not directly related to the base application 132, but provide additional functions or features which may be useful to particular groups of users.

Consolidated software application 130 may further include hardware connectivity software 140. The hardware connectivity software 140 is used to communicate with external devices. In an illustrative embodiment, the external devices are physiological devices such as glucose meters, infusion pumps, cellular phones, instant messaging devices, fax machines, e-mail devices, data modems, personal data assistants (PDAs), or integrated devices including a glucose measurement engine and PDA or cellular device.

Figure 3:
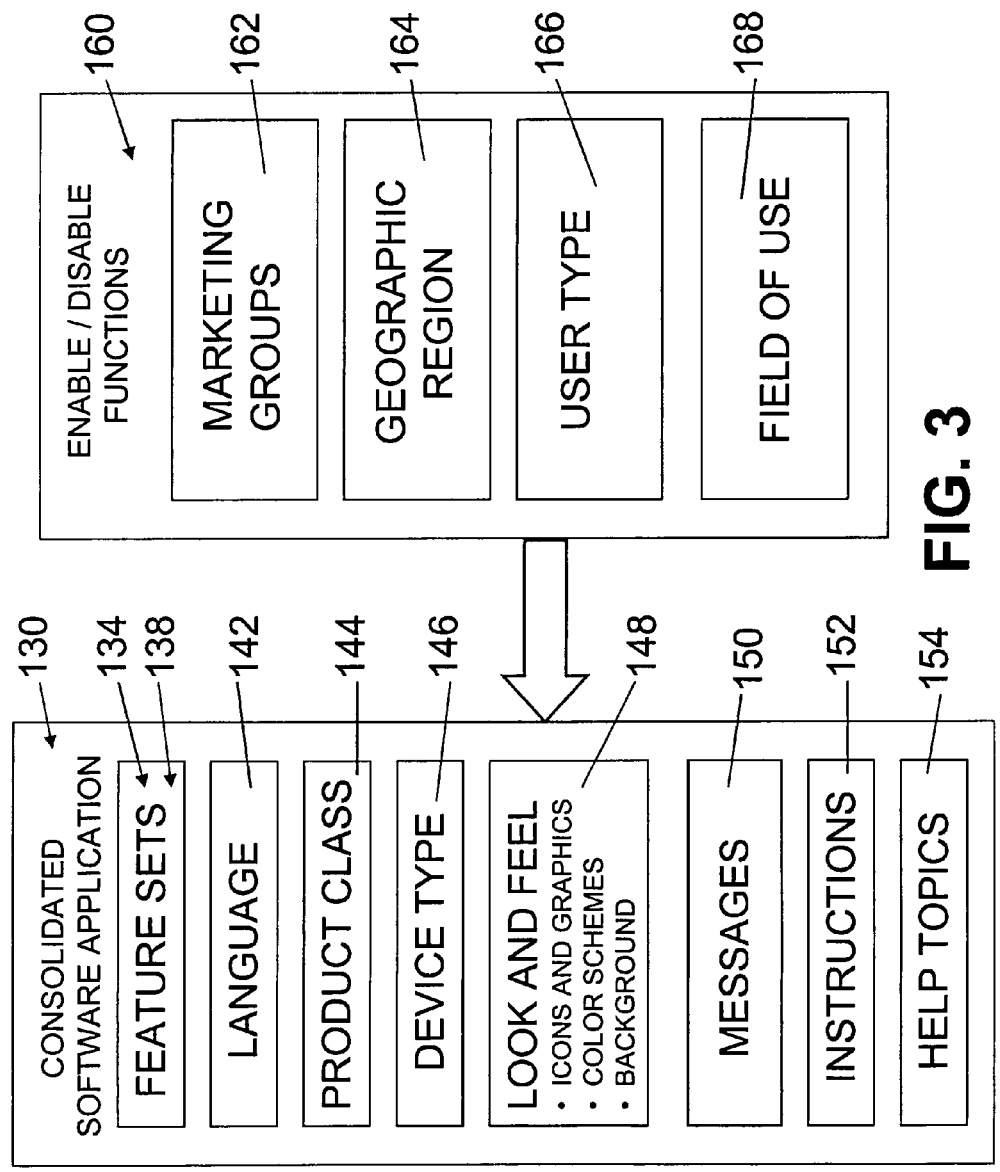
FIG. 3 is a block diagram illustrating features and functions of the consolidated software application and different factors considered for selectively enabling and disabling certain of the features and functions.

Additional features of the consolidated software application 130 are illustrated in FIG. 3. The entire consolidated software application 130 is illustratively delivered to all types of users. Certain features and functions of the consolidated software system 130 are selectively enabled or disabled depending upon certain factors discussed herein. As shown in FIG. 3, the consolidated software application 130 includes both the dependent feature sets 134 and stand alone feature sets 138 discussed above. In addition, the consolidated software application 130 supports many different languages for use on a display of a user interface and in reports generated by the application 130 as illustrated at block 142.

The consolidated software application 130 further includes software applicable to different product classes 144. For example, different software may be provided for consumers, healthcare providers, insurance companies or other payors, managed care providers, health maintenance organizations (HMOs) or the like.

A standard mode and a test mode of operation are available for each of the different product classes. Consolidated software application 130 further supports multiple device types as illustrated at block 146. For example, the consolidated software 130 may include different software to support different types of glucose meters and infusion pumps in one illustrated embodiment. Software for multiple device types may be provided for both the device programming software 136 and the hardware connectivity software 140 discussed above. In addition, the dependent feature sets 134 and stand alone feature sets 138 may be device specific.

The consolidated software application 130 includes a plurality of components to adjust the look and feel of the software during operation as illustrated at block 148. For example, multiple types or styles of icons, graphics and color schemes used on screen displays of a user interface are provided so that the look and feel of the software can be customized for different users. Different background images may also be provided for selection for different users. In addition, different measurement units may be used for the physiological information. For example, for blood glucose measurement, certain users may prefer to measure blood glucose in mg/dL while other users may prefer to measure blood glucose in mmol/L.

Consolidated software application 130 also includes multiple different types of messages as illustrated at block 150. In addition, consolidated software application may include various types of instructions as illustrated at block 152 and help topics as illustrated at block 154. The messages 150, instructions 152 and help topics 154 are unique for the different feature sets, language, product class and device types and may be selectively shown on the display of the user interface depending on which features and functions are active and enabled.

The consolidated software application 130 therefore provides a single software application that can be distributed to multiple types of users and support multiple devices throughout the world. The consolidated software application 130 is then configured to activate and/or enable selective features and functions as discussed below to customize the consolidated software application 130 for particular users and devices.

The system and method of the present invention permits multiple levels of customization or activation of the features and functions as illustrated at block 160 in FIG. 3. The first level of customization is provided, for example, by marketing groups for the consolidated software application 130 as illustrated at block 162. In one illustrated embodiment, a marketing group may be a marketing manager or marketing team for a particular country. In other examples, the manufacturer may be the marketing group along with sales representatives from certain countries. Therefore, features and functions of the consolidated software application 130 may be active or inactive, enabled or disabled based on preferences from the marketing groups 162. Certain of these preferences may be based on geographic regions as illustrated at block 164.

Different user types are also considered when enabling and disabling features and functions of the consolidated software application 130 as illustrated at block 166. The different user types may include, for example, consumers, healthcare professionals, managed care providers, health maintenance organizations (HMOs) or payors such as insurance providers. The users may be standard users or they have administrative rights over the consolidated software application 130. There may be multiple different types of healthcare professionals each of which may be classified as a different user type, if desired.

The enabling and disabling of functions may be further controlled based upon the field of use for the consolidated software application 130 as illustrated at block 168. As discussed below, activation keys and enabling and disabling of active features by system administrators control operation of the consolidated software application 130 to support field of use license agreements.

Figure 4:
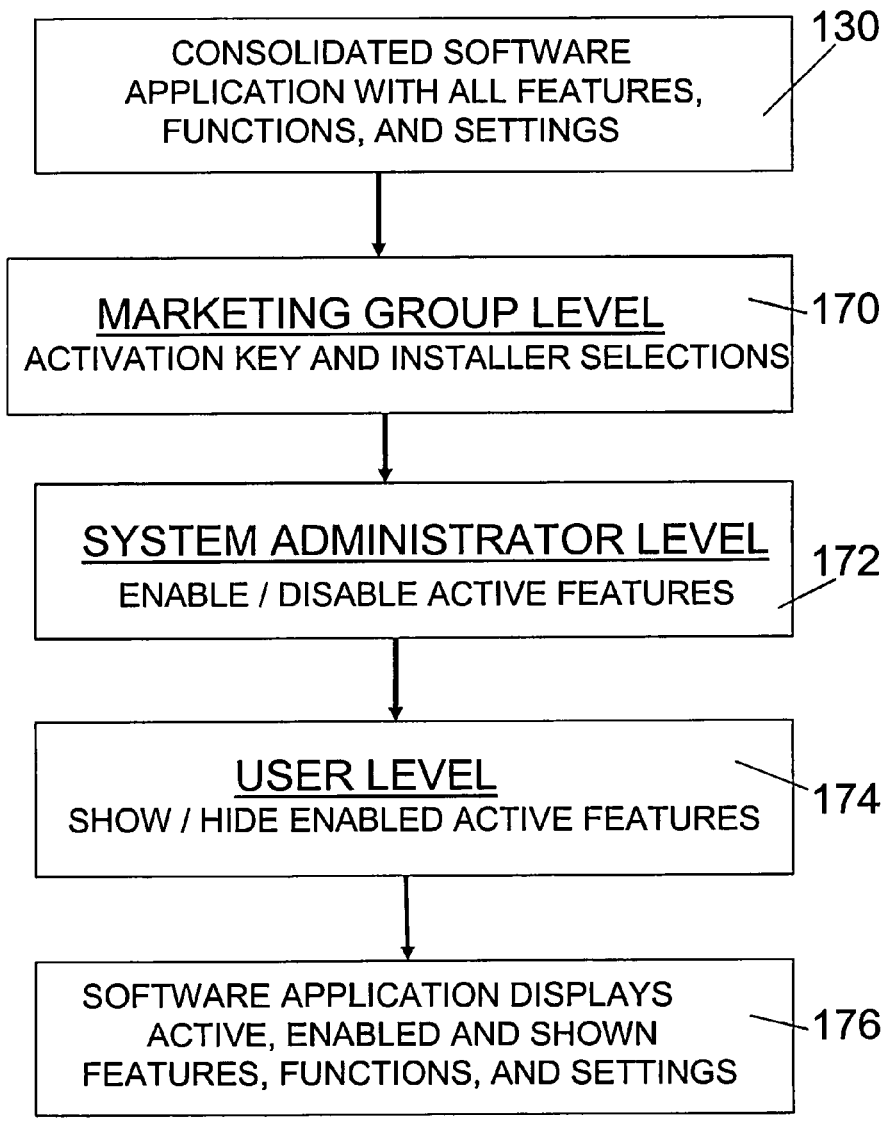
FIG. 4 is a flow chart further illustrating the customization of the consolidated software application in accordance with the present invention.

FIG. 4 further illustrates the multiple levels of customization of the consolidated software application 130. As discussed above, the consolidated software application 130 is delivered to all types of users in the same format such as on a CD or DVD or other memory device such as a memory stick. It is understood that the consolidated software application could also be transmitted to the users via a communication network, such as by downloading the consolidated software application 130 over the Internet.

Block 170 of FIG. 4 illustrates a first level of customization of the consolidated software application 130. For illustrative purposes, block 170 refers to the marketing group level customization. A manufacturer and/or marketing manager for a particular region, for example, may cooperate to configure the consolidated software application 130 for a particular geographic region, user type, or field of use. In the illustrated embodiment, this initial configuration is illustratively accomplished using a plurality of different activation keys and installer selections which selectively activate certain features and functions illustrated in the consolidated software application 130 of FIGS. 2 and 3. The marketing group level customization illustratively provides configuration data which establishes certain parameters during installation of the consolidated software application 130 based on, for example, an activation key or other suitable method. These parameters established by the configuration data cannot be modified by the end user or an administrator for the end user without reinstallation of the consolidated software application 130 using a different activation key or different answers to preliminary questions provided by an installer during installation. The activation keys selectively activate certain feature sets 134, device programming software 136, stand alone feature sets 138, and hardware connectivity software 140 as established by the manufacturer, owner, marketing director, or the like. The activation keys may also selectively activate any of the features and functions set forth in block 130 of FIG. 3, or other desired features and functions.

In an illustrative embodiment, if features or functions are not activated with the activation key, these features and functions are not visible on a display 104 of a user interface when the software application 130 is executed by the end user or system administrator. In other words, the end users and system administrators using the consolidated software 130 do not even know that certain features and functions which have not been activated are available on the consolidated software application 130. References to the non-active features are not included on the display device 104 of the computing device 102. This marketing group level customization illustrated at block 170 is particularly helpful as marketing directors and sales representatives determine that particular features may be either important or not important within their particular regions or geographic areas. For example, if the marketing manager in a certain country determines that feature set 2 shown in FIG. 2 is confusing to people in that particular geographic region, a new activation key can be created to disable feature set 2 from all of the consolidated software applications 130 used in the particular geographic region. By updating the activation key, the feature can be removed from the system actually operated by the users within the specific geographic region without having to distribute a new software application.

During installation, certain questions are asked to further customize the consolidated software application as discussed in detail below. For instance, the language used on the display 104 and in reports generated by the application 130 may be selected by an installer. Units of measure or other parameters may also be selected. The next level of customization is illustratively the system administrator level as illustrated at block 172 in FIG. 4. Once the active features and functions have been loaded onto computing device 102, the system administrator has the ability to selectively enable and disable certain of the active features. Once again, any features that were not activated by the activation keys are not shown on the display of the user interface accessible by the system administrator. Therefore, the computing device 102 does not display information related to the non-active features, even to the system administrator.

Features enabled (or not disabled) by the system administrator become part of the active and enabled features and functions available to the end user of the software application 130 such as the consumer, healthcare professional, managed care provider, health maintenance organization or insurance provider. If the system administrator disables certain active features at block 172, then these features are hidden from the end users. For example, if the system administrator decides to disable feature set N and stand alone feature sets 138 illustrated in FIG. 2, these disabled feature sets N and 138 are not referenced on the display device 104 of the user interface accessible by the end user during operation of the software application 130. Therefore, the end user does not even know that the disabled features and functions are available on the consolidated software application 130.

In the present invention, the end user also has the ability to show and hide certain enabled active features during operation of the software application 130 by the end user as illustrated in block 174 of FIG. 4. Once the end user has selected to hide a certain feature or function, references to the hidden feature or function are removed from the display 104 of the user interface during normal operation of the software. Hidden features and functions are still shown at a location (such as a Preferences screen) which permits the selecting of which features to show and hide as discussed below. Therefore, the software application 130 actually run by the end user displays only active, enabled and "shown" features, functions and settings as illustrated at block 176 in FIG. 4.

The consolidated software application 130 in one illustrated embodiment is a diabetes information management application that comprises a number of related software applications. Blood glucose, abbreviated bG, is an important physiological parameter for diabetic patients. It is a measurement of glucose or sugar levels in the patient's blood. Blood glucose levels are measured regularly and frequently using a type of medical device such as a glucose meter. Patients control blood sugar levels through medication, diet, physical activity, and other behaviors. The system 100 receives medical data, including bG data, pertaining to these variables and may display the data in statistical, tabular, or other forms to ease interpretation. Similarly, the software may receive medical data pertaining to any of a plurality of physiological conditions of the patients and related medical devices.

In an illustrated embodiment, the consolidated software application 130 is designed for consumers who need to evaluate their diabetes information, for health care professionals who need to evaluate diabetes information from and for patients, and other users such as insurance companies or other payors. As discussed above, the consolidated software application 130 includes all the features and functions to support these various end users in a single software package.

In a consumer environment, the users are patients (those with diabetes) and their caregivers. In a Professional environment, the users are doctors, diabetes nurse educators (DNEs), office staff, and, in some cases, the patients. In a Payor environment, the users are insurance company employees. For convenience, this application refers to the first type of user as "Consumers", the second as "Professionals" and the third as "Payors" even though the groups are broader than these terms may suggest.

The consolidated software application 130 may be used in a plurality of different use environments. In the consumer environment, the computer 102 on which the consolidated software application 130 is installed may be used for a variety of purposes, both personal and possibly business, and may be used by more than one person. The computer 102 may be turned off between uses. The consolidated software application 130 may be installed by the Consumer, or by a third party who is not a user of the application. The task urgency is low and the need for the user to multi-task is minimal.

In the Professional environment, the computer 102 is typically used for other purposes in support of the office. These other uses may include, for example, patient scheduling, record management and retrieval, and word processing. Users will range from highly technical and computer literate, to non-technical and only moderately computer literate. Many Professional installations will be in a networked environment. Professional installations are expected to have a printer, fax and e-mail capabilities.

An exemplary embodiment of the present invention will now be described in connection with a diabetes management system. As discussed above, the same consolidated software application 130 is distributed to all user types in all geographic regions. The consolidated software application 130 is then installed onto users' computer system 102.

Figure 5:
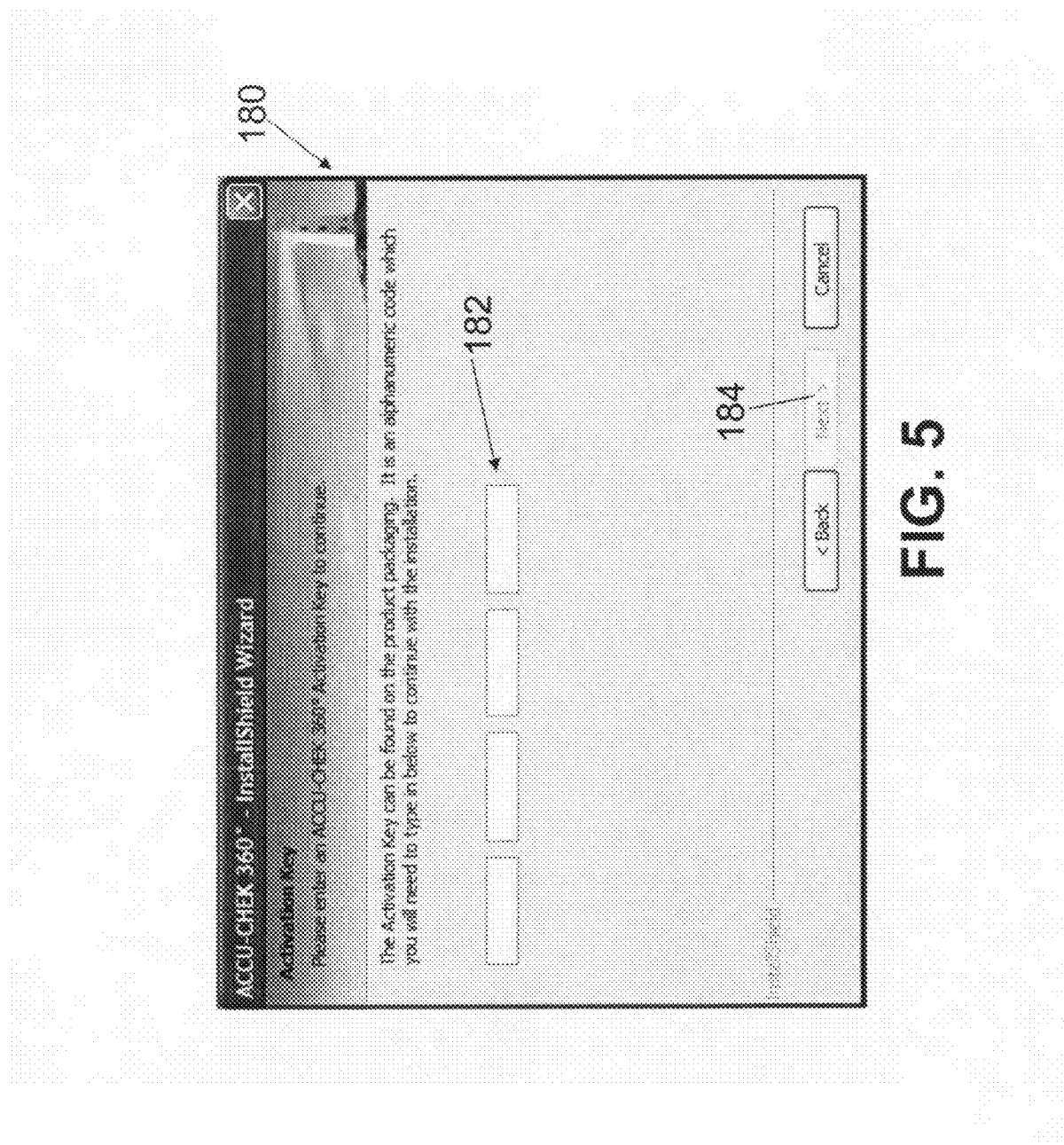
FIG. 5 is an exemplary activation key input screen of a user interface used during installation of the consolidated software application.

The installer is prompted for an activation key as illustrated at screen 180 shown in FIG. 5. Typically, the activation key is sent along with the product packaging, but may be sent separately. In the illustrated embodiment, the activation key is an alpha numeric code which is entered in the appropriate location 182 on display screen 180. After entering the activation key, the installer then clicks the "Next" button 184.

The activation key is one illustrative method by which the consolidated software application 130 controls specific aspects of the application such as the market in which the product is placed, the features enabled, the trial period for the application, and the like. In an illustrated embodiment, the activation key provides groups of alphanumeric characters which are entered by the installer during installation. The alphanumeric characters represent a series of ones and zeros corresponding to features and functions of the consolidated software application 130. A logical one associated with a feature or function indicates that particular feature or function is active.

The activation key automatically activates identified features and functions of the software application 130 without requiring the installer to make a large number of entries. Illustratively, the activation key contains information related to product identification, product class, trial mode days, the version of the application, marketing group information, feature set information, and integrity information. The product identification may be, for example, a character such as a number or letter to identify the particular product such as, for example, the ACCU-CHEK 360 application available from Roche Diagnostics Corporation. The product class is illustratively identified as the type of use or user to which the key belongs. For example, a number or letter may be used to designate the particular product class. The product class information is used as a verification that the key is correct for the product being installed, or to automatically select the class when classes are merely different modes of the product. Product class examples include the standard consumer class, the standard consumer test mode, the professional class, the professional class test mode, the payor class, and the payor class test mode. The trial mode days portion of the activation key represents the number of days the product is allowed to operate in a trial mode. Again, numbers or letters may be used to represent the number of days for the trial mode. If the number of trial mode days is set to zero, the key indicates that there is no expiration date and therefore the product has been purchased or licensed. The version information is used so that old keys are not "valid" on newer versions of the software. A CRC, checksum, or other integrity information may be included in the key to detect erroneous entries.

Marketing Group information illustratively represents the countries where the key is valid (Included Markets) and where the key is not valid (Excluded Markets). Typically, ISO 3166 country codes are used to identify particular market groups by region. The format of the Marketing Group information is illustratively as two groups (Included and Excluded Markets) of two characters.

The feature set information of the activation key is illustratively hexadecimal characters (0-9 or A-F) which represent all the potential combinations of distinct feature sets. Each feature set is illustratively defined as a bit location and the value of the bit indicates it state, "1" being active and "0" being non-active. This key is used to indicate whether or not to install the feature set, or whether to provide access (i.e. enable) the feature set. It is understood that Binary Coded Decimal (BCD) or Octal (base-8) values may also be used for key characters.

Figure 6:
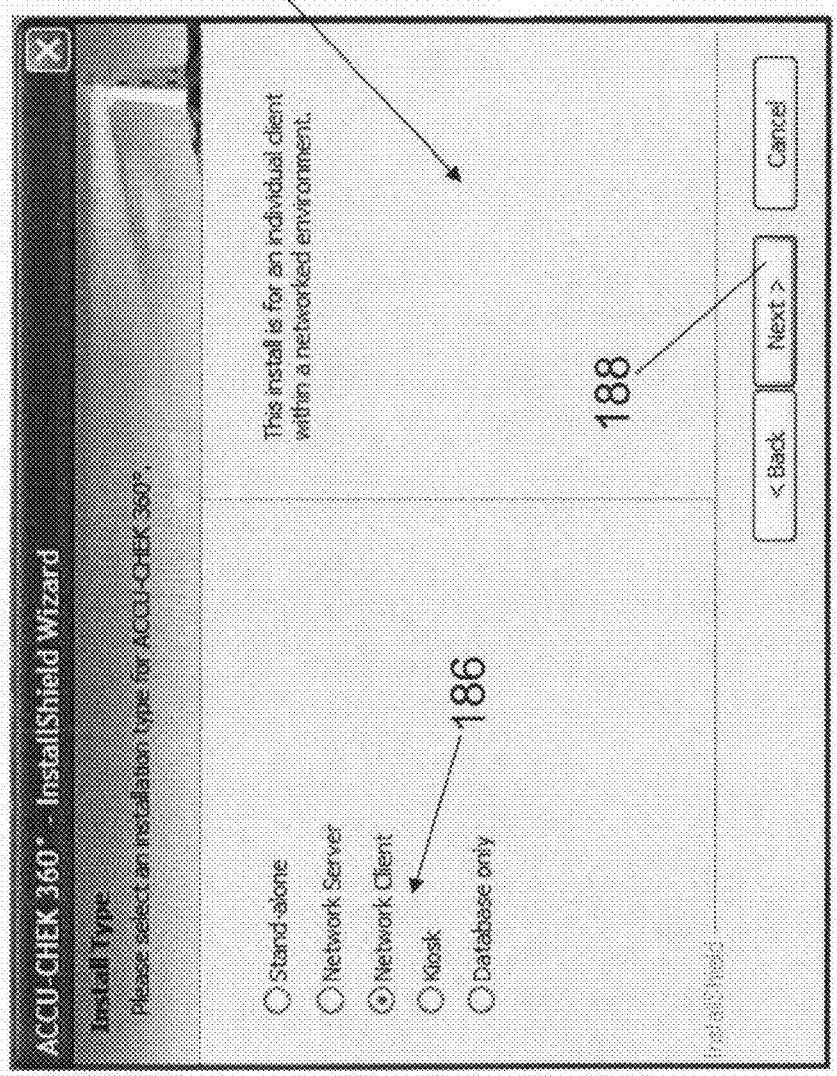
FIG. 6 is an exemplary screen of the user interface to select a type of device on which the consolidated software application is to be installed.

After the activation key is entered as shown in FIG. 5, the installer is next prompted to enter the type of system on which the consolidated software application 130 is to be installed as illustrated by screen 185 in FIG. 6. The user selects the appropriate entry in region 186 and then click the "Next" button 188. Depending upon the installation type selected, the consolidated software application 130 may activate different features or functions. As shown in FIG. 6, illustrative install types are stand-alone, network server, network client, kiosk, and database only.

Figure 7:
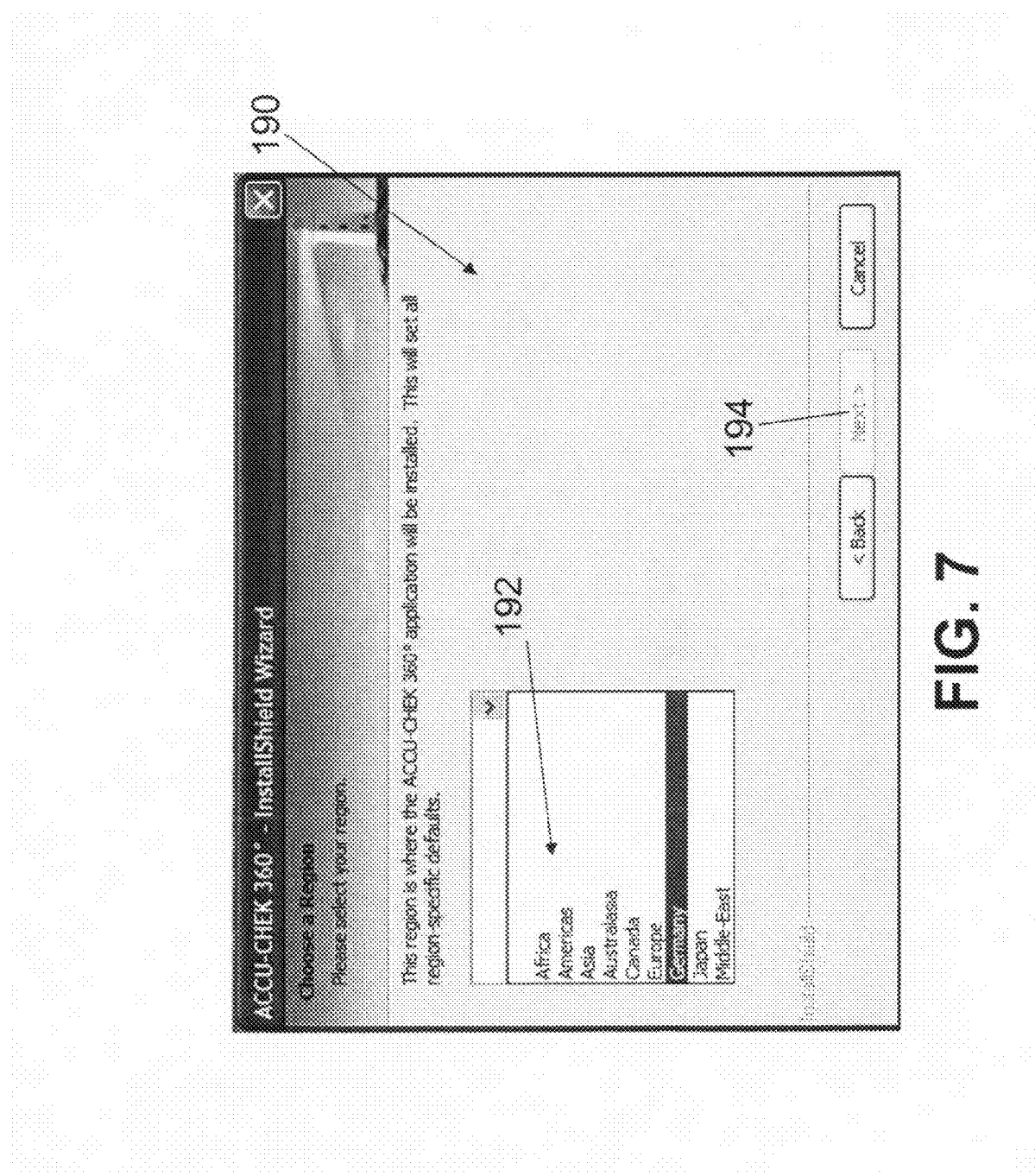
FIG. 7 is an exemplary screen of the user interface to permit selection of the geographic region in which the consolidated software application will be installed.

Next, screen 190 in FIG. 7 is displayed on the user interface. Installer selects the geographic region in which the application will be installed from a drop down menu 192 or other selection or entering method. Once the appropriate region is selected, the "Next" button 194 is selected. Selecting the geographic region sets region-specific defaults within the consolidated software application 130. For instance, the look and feel of the software (see block 148 in FIG. 3) may be changed based on the specific geographic region selected. In addition, any of the consolidated software application 130 features and functions showing in FIG. 2 or 3 may be activated based on the selected geographic region based on input from marketing groups for the application 130.

Figure 8:
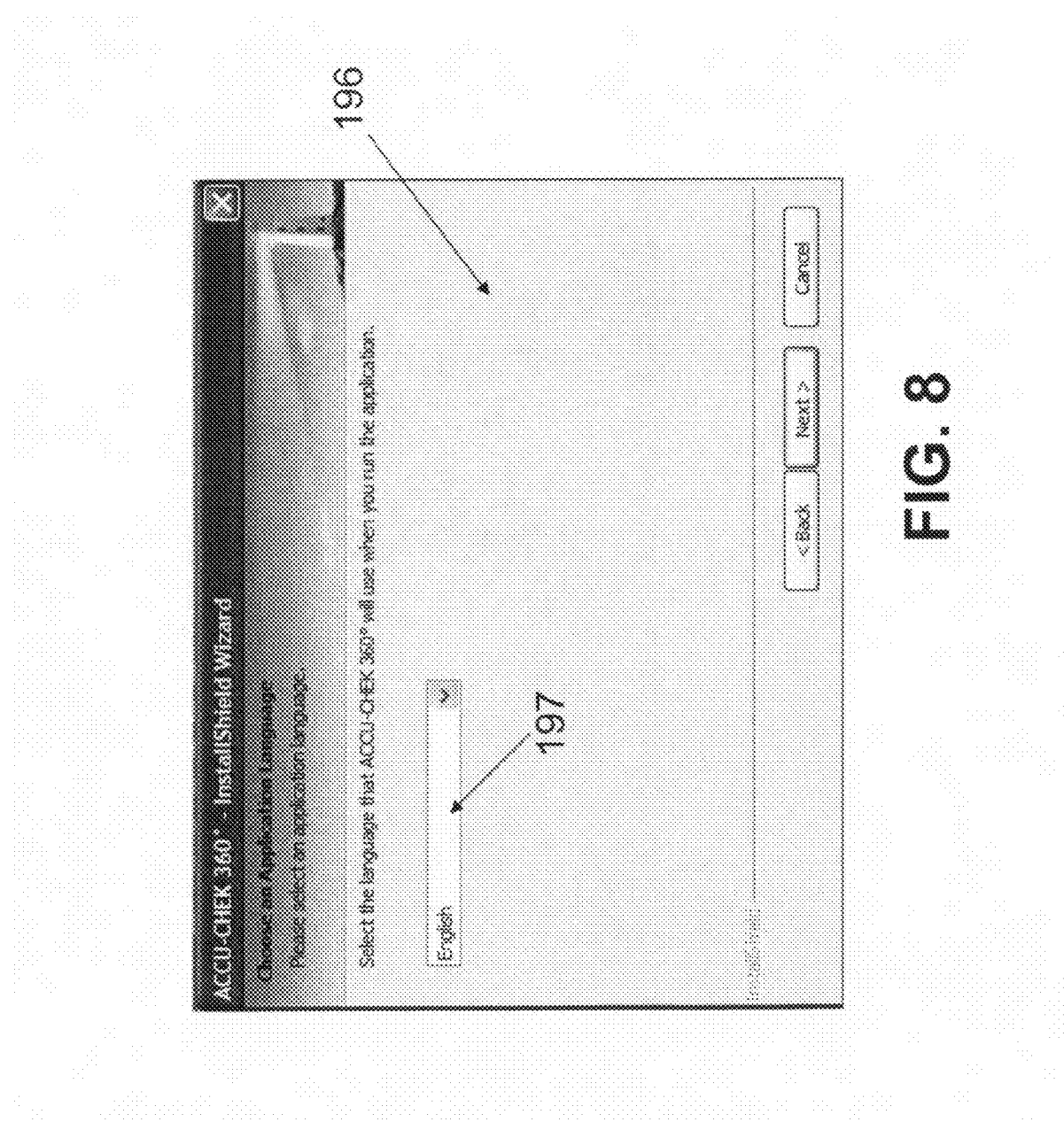
FIG. 8 is an exemplary screen of the user interface to permit selection of the language used during operation of the consolidated software application.

The installer then selects the language to be used when the software application is run as illustrated at screen 196 in FIG. 8. Illustratively, a drop down selection menu may be used as illustrated at location 197.

Figure 9:
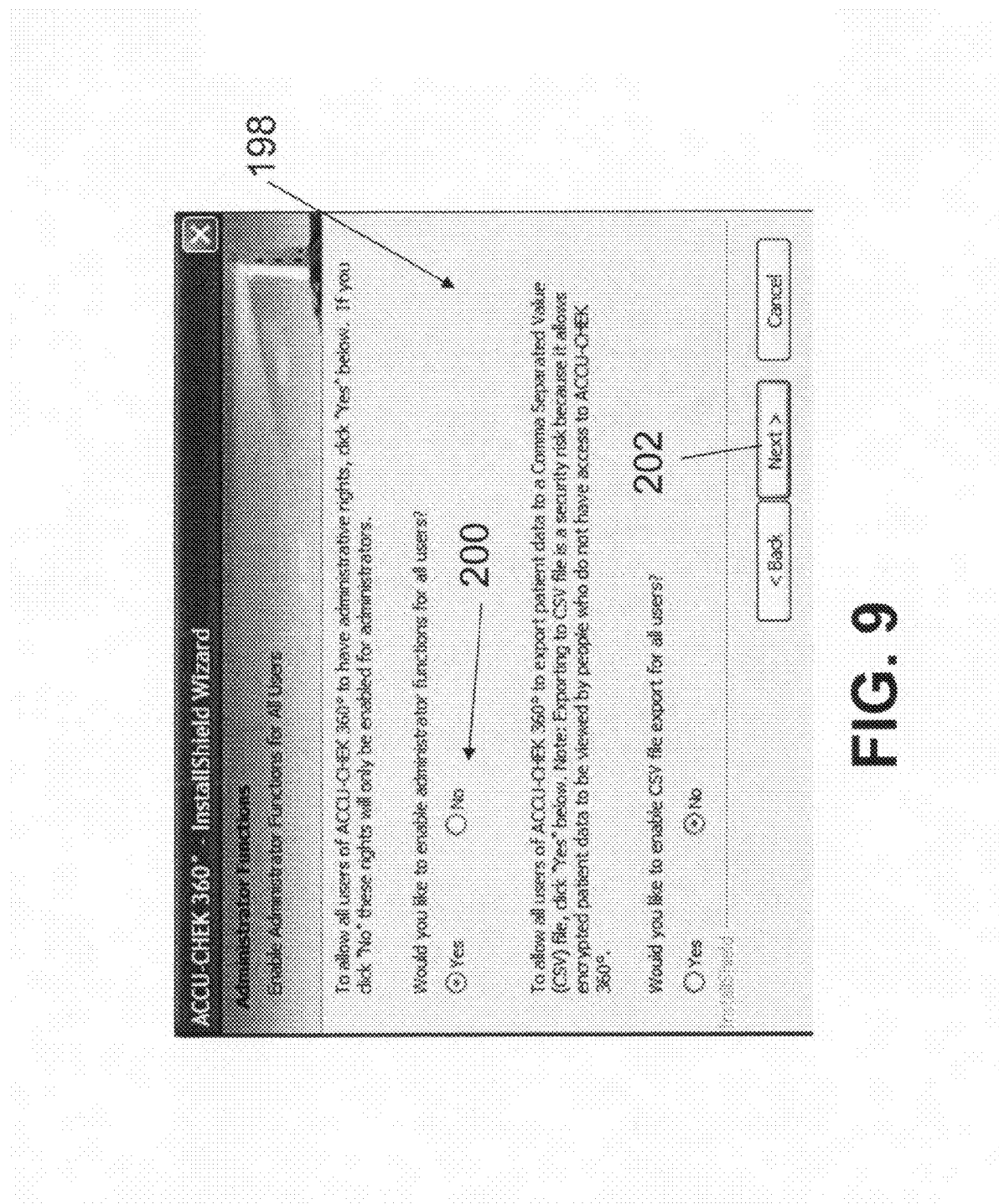
FIG. 9 is an exemplary screen of the user interface to permit selection of administrator functions.
Figure 10:
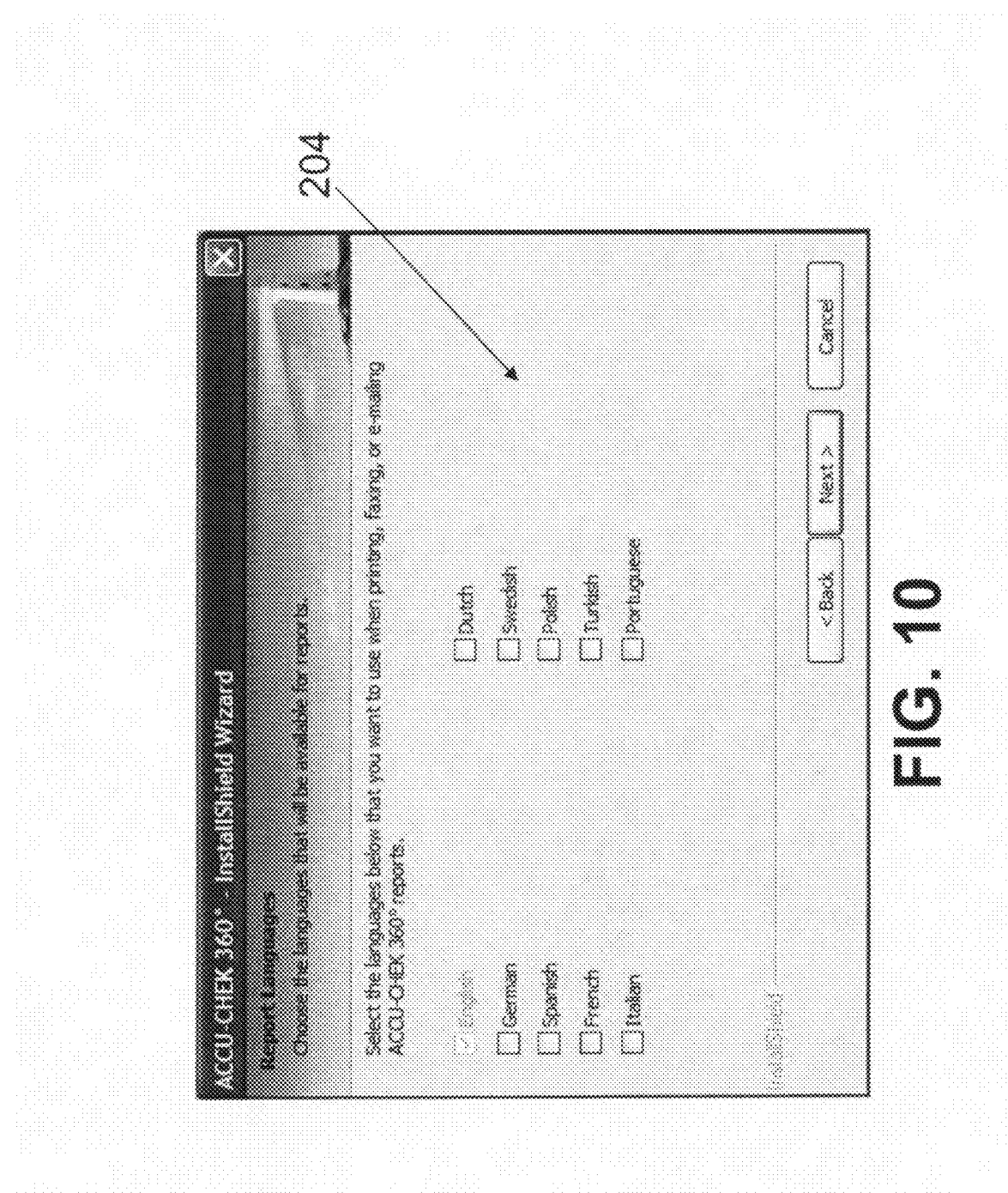
FIG. 10 is an exemplary view of the user interface to permit selection of languages for reports generated by the consolidated software application.

Next, the installer sets certain administrative functions as illustrated at screen 198 in FIG. 9. For instance, the installer can decide whether or not all users of the software application will have administrative rights or whether only certain users may be designated as system administrators as illustrated at location 200. Once the installer selects the administrative functions at screen 198 and selects the "Next" button 202, the installer selects the languages that will be available for generated reports when printing, faxing or e-mailing such reports as illustrated at screen 204 of FIG. 10. More than one language may be selected on screen 204.

Figure 11:
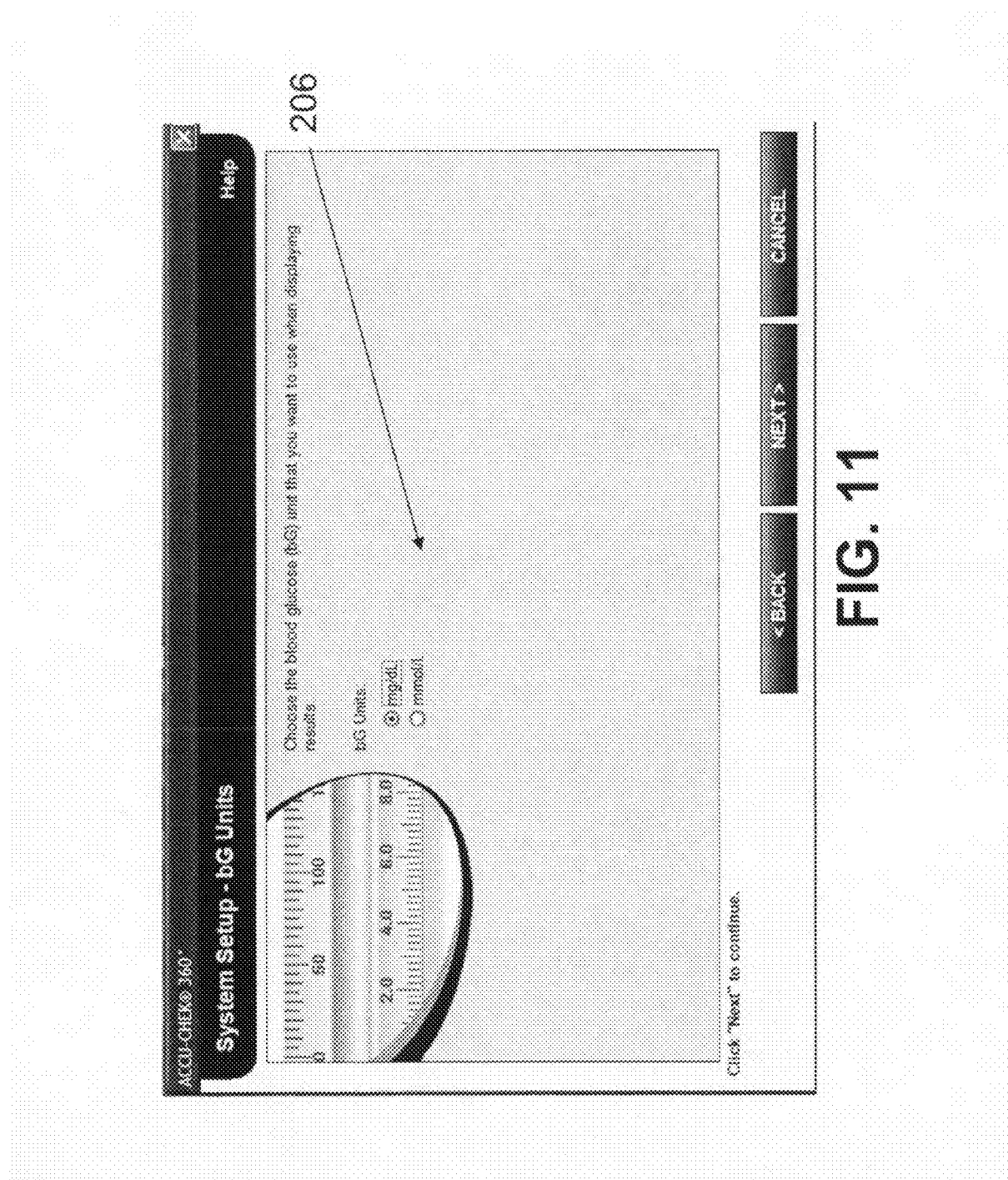
FIG. 11 is an exemplary screen of the user interface to permit selection of units of measure used in the application.

The system installer also select the units of measurement for blood glucose as illustrated at screen 206 in FIG. 11. It is understood that other units of measure for other physiological information discussed herein may also be selected during installation.

Figure 12:
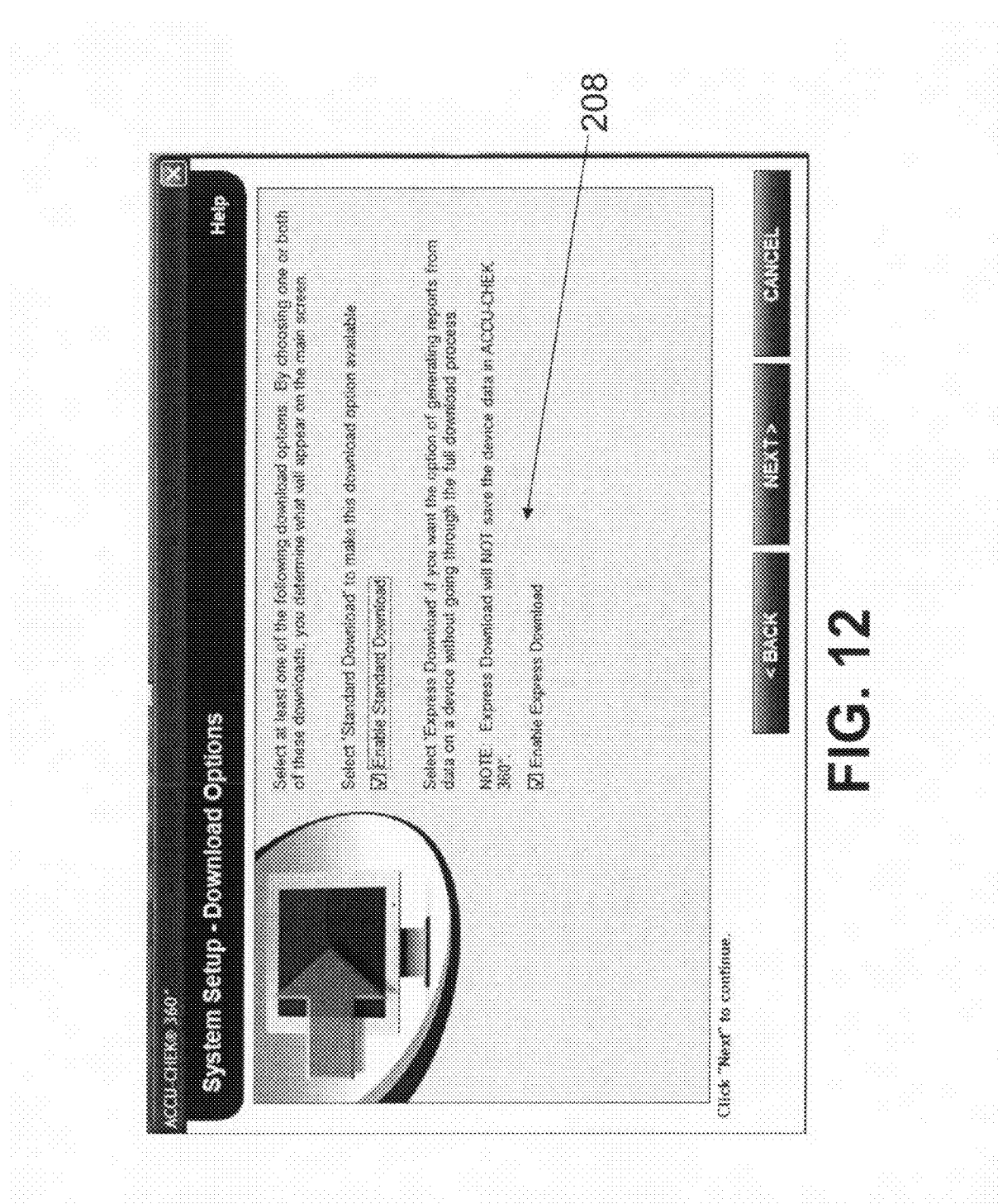
FIGS. 12 and 13 are exemplary screens of the user interface to permit enabling and disabling of certain features and functions of the consolidated software application during installation.
Figure 13:
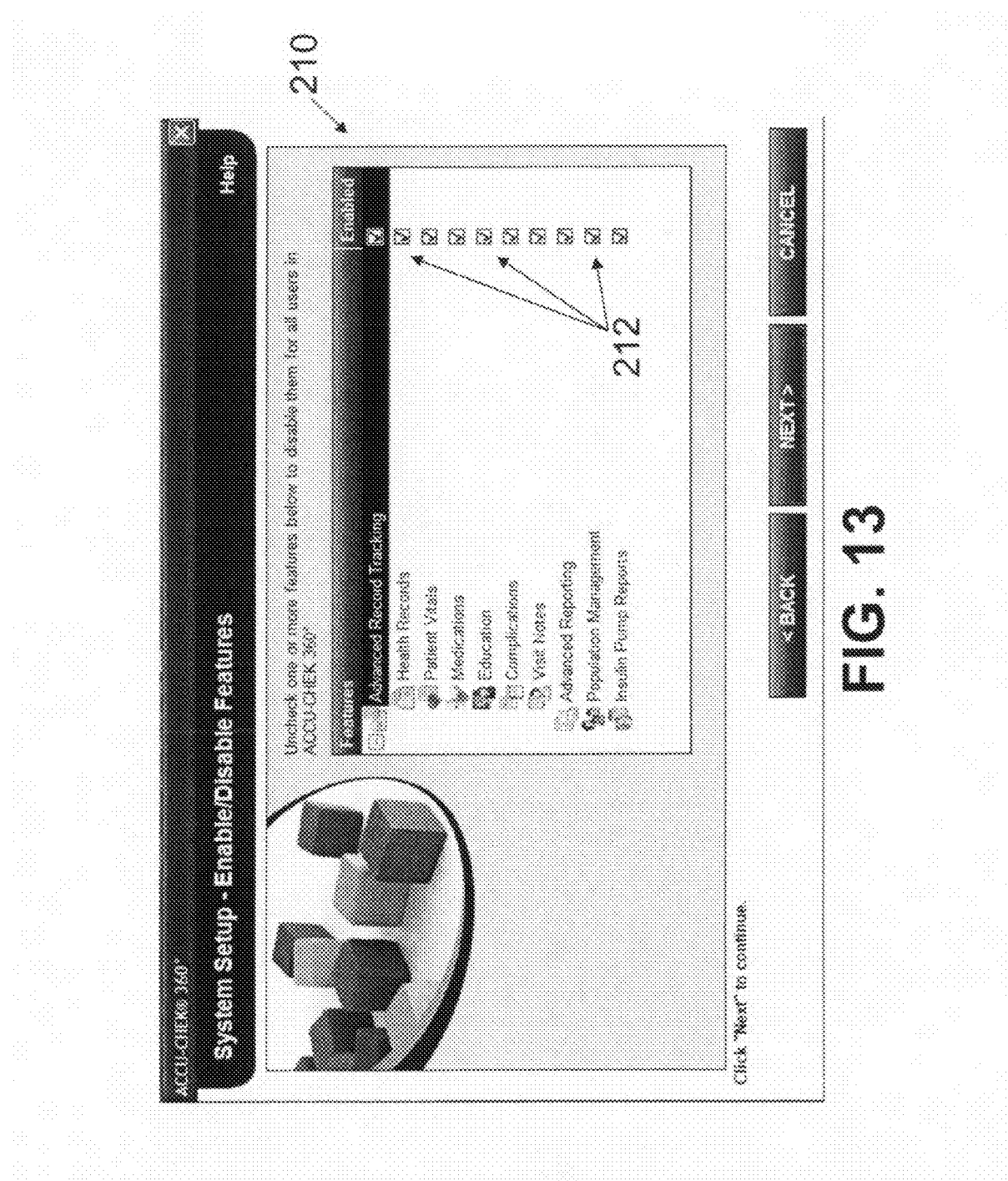

The installer then may select whether or not certain features are enabled or disabled in the installed software application as illustrated in FIGS. 12 and 13. One example of enabling and disabling features is shown at screen 208 in FIG. 12. For example, the installer may select whether or not to enable a "Standard Download" or an "Express Download". In the illustrated embodiment, the "standard download" saves all information downloaded from the medical device 120 in the memory of computing device 100. The "express download" enables the printing of reports during the download process but does not save the download information in the memory of computing device 100. If either of the standard download or express download are not enabled at screen 208, references to the disabled feature will not appear on the display of the user interface during operation of the software application 130 unless the application is reinstalled and the feature is enabled.

Screen 210 of FIG. 13 illustrates that the system installer may selectively disable certain features of the software system by unchecking the "Enabled" box corresponding to the particular feature as illustrated at locations 212 in FIG. 13. For instance, if "Insulin Pump Reports" is disabled by removing the check in the corresponding box, nothing related to "Insulin Pump Reports" will be provided on the displays of user interfaces available to either system administrators or end users once installation of the consolidated software application 130 is complete. To obtain the "Insulin Pump Reports", the software application 130 must be reinstalled to enable the "Insulin Pump Reports" feature by checking the appropriate box 212 at screen 210 of FIG. 13.

Figure 14:
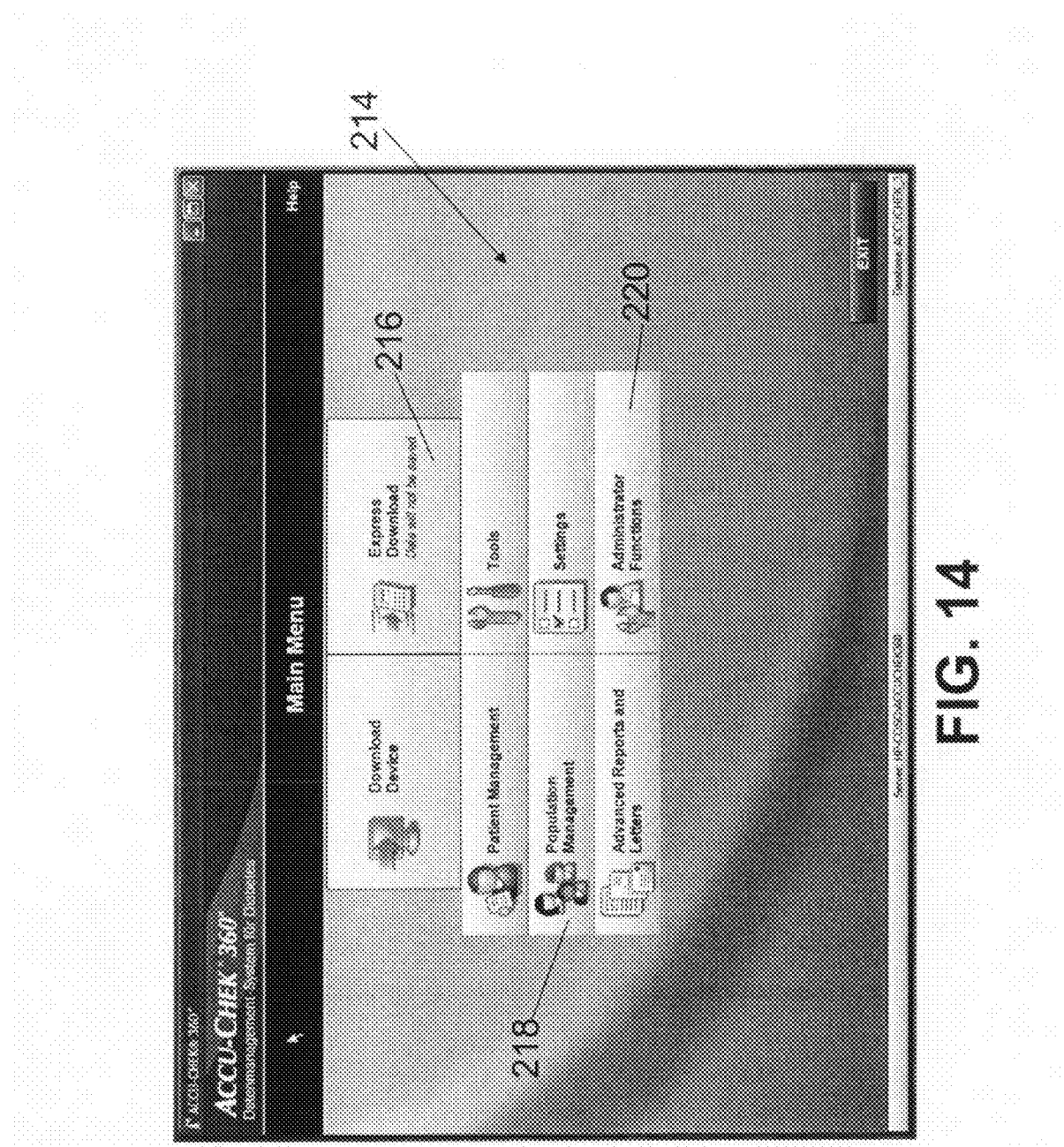
FIG. 14 is an exemplary main menu screen of an user interface of a healthcare management software system.

Once installation of the software application 130 is complete, a main menu is presented as illustrated at screen 214 of FIG. 14. Features which were activated by the activation key and left enabled during the installation process are displayed on the main menu on screen 214. If certain of the features were either not activated by the activation key or disabled during installation, then those features would not be displayed on the main menu on the user interface. For instance, if the "Express Download" was disabled at screen 208 of FIG. 12, the "Express Download" icon 216 on screen 214 would not be visible. Similarly, if the "Population Management" feature was disabled at screen 210 of FIG. 13, the "Population Management" icon 218 on screen 214 would not be shown since this feature would not be available in the installed version of the software.

Figure 15:
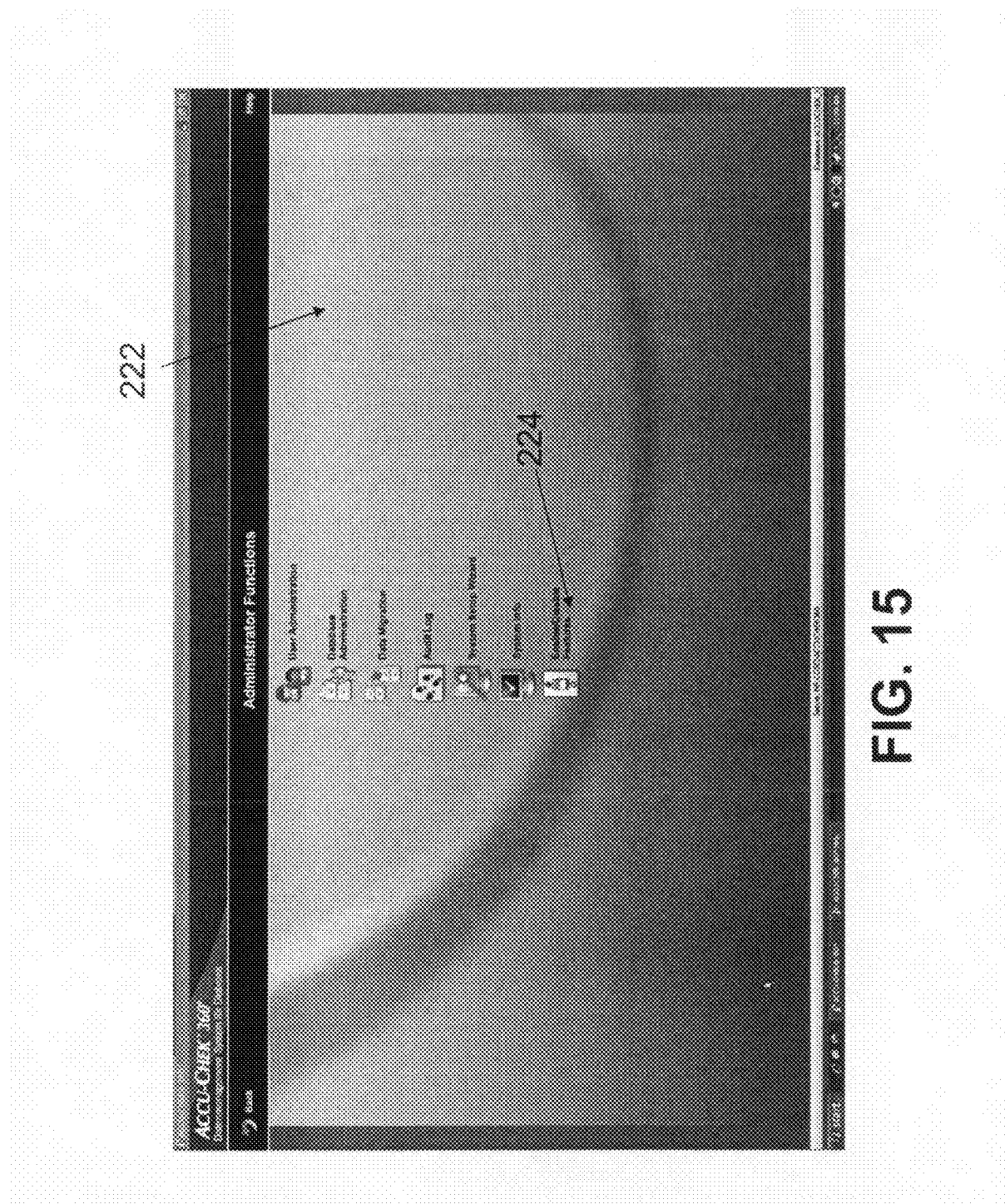
FIG. 15 is an exemplary administrator function screen of the user interface of the healthcare management software system.
Figure 16:
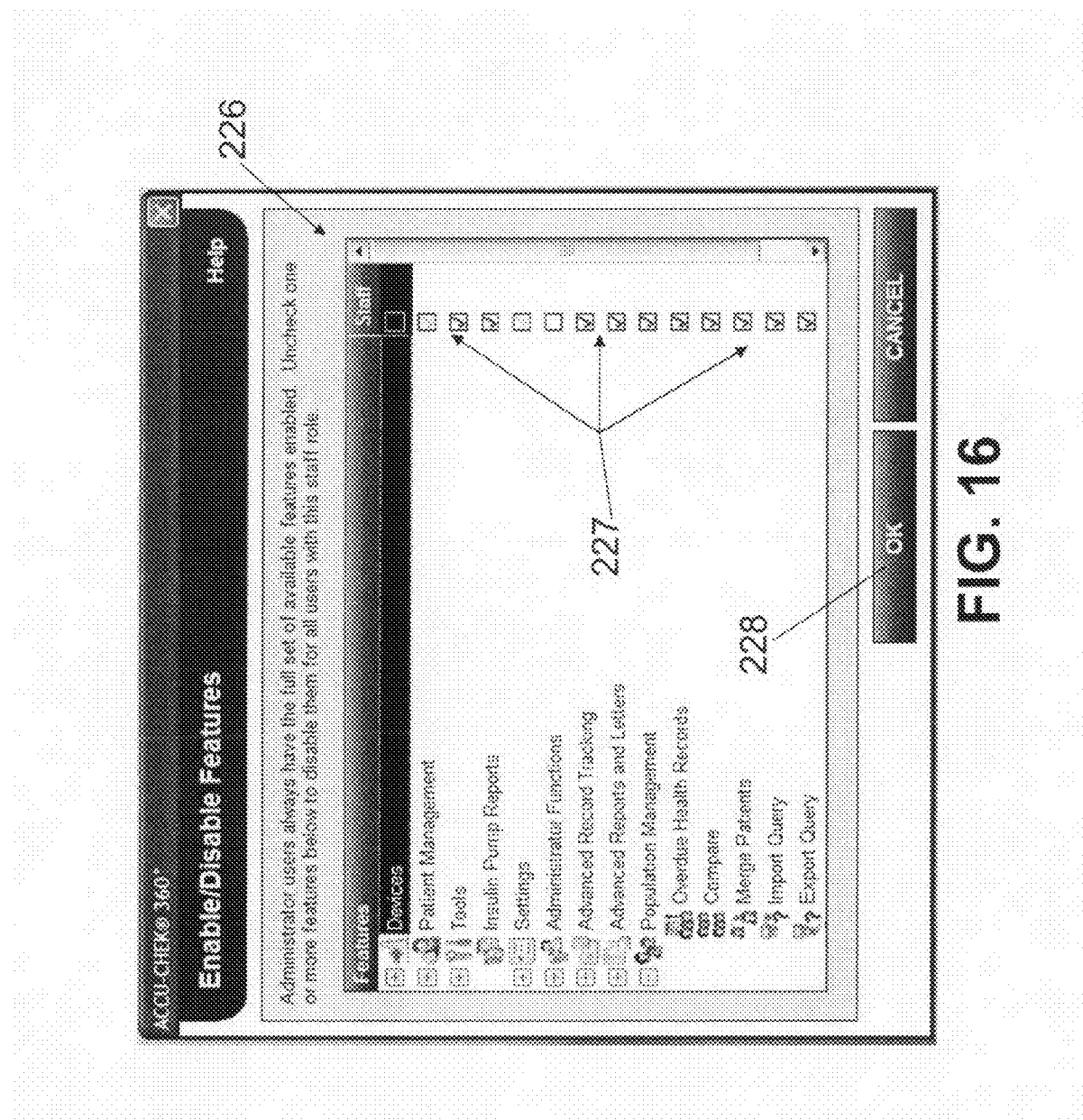
FIG. 16 is an exemplary enable/disable features screen of the user interface accessible by a system administrator of the healthcare management software system.

If an administrator clicks the "Administrator Functions" icon 220 on screen 214, screen 222 of FIG. 15 is displayed on display 104 to show the active and enabled "Administrator Functions". If the administrator clicks the "Enable/Disable Features" button 224 in FIG. 15, screen 226 shown in FIG. 16 is displayed on display 104. The administrator can then enable or disable certain features which were activated by the activation key and enabled during the installation process. Therefore, administrator can select additional features to include or remove from the software application as operated by end users as discussed above in connection with block 172 of FIG. 4. In the illustrated embodiment, the administrator may make click on the selection boxes 227 to check or uncheck the box corresponding to certain features which may be enabled or disabled by the administrator. After the administrator has selected which features to enable or disable on screen 226, the administrator clicks the "OK" button 228 in FIG. 16. If features are disabled at screen 226, reference is not made to these features on the user interface display 104 when the end user operates the software application 130.

Figure 17:
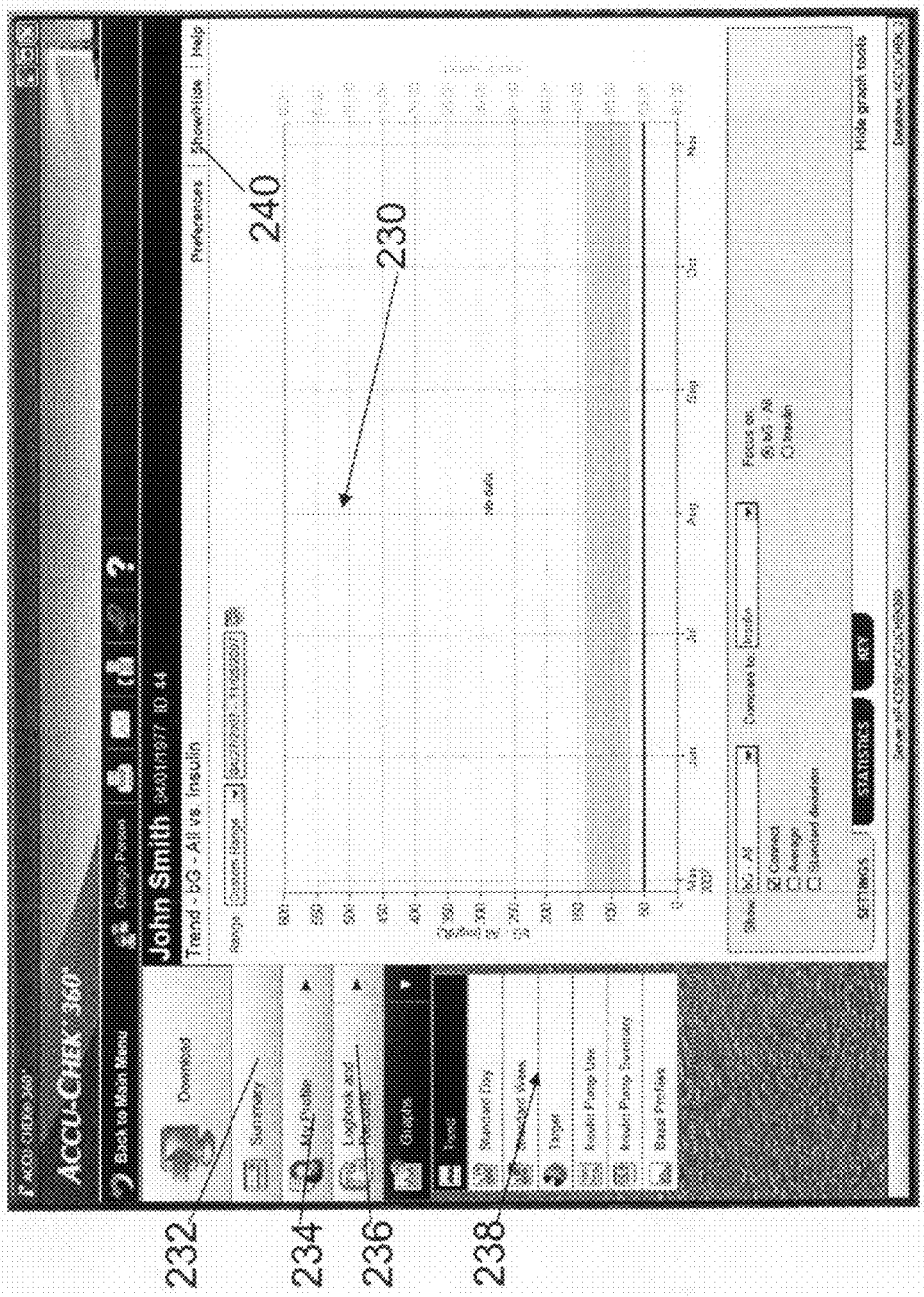
FIG. 17 is a patient healthcare information screen on the user interface illustrating active and enabled features and functions of the consolidated software application available to an end user.
Figure 18:
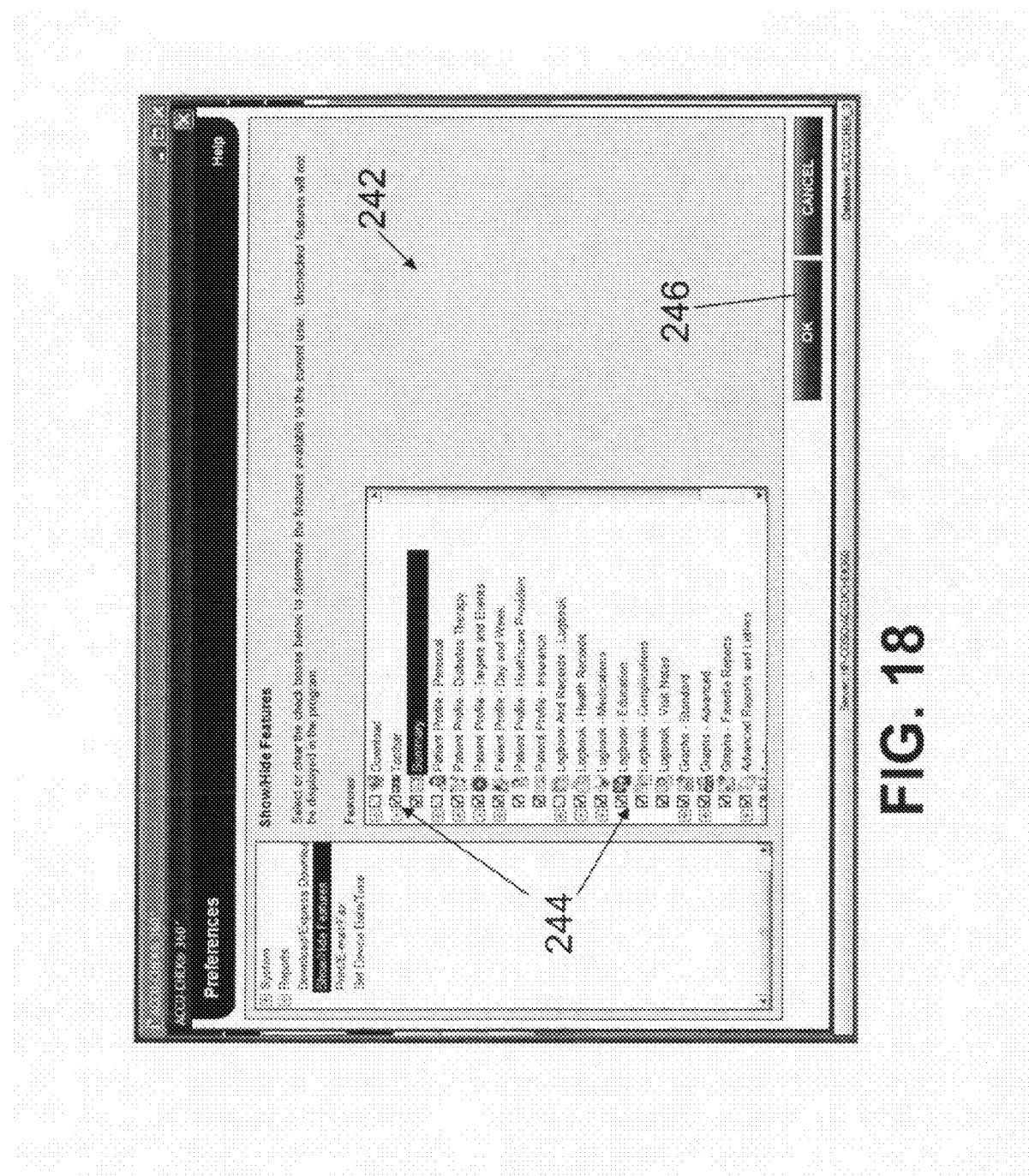
FIG. 18 is an exemplary screen of the user interface allowing the end user to show and hide certain features and functions of the consolidated software application.
Figure 19:
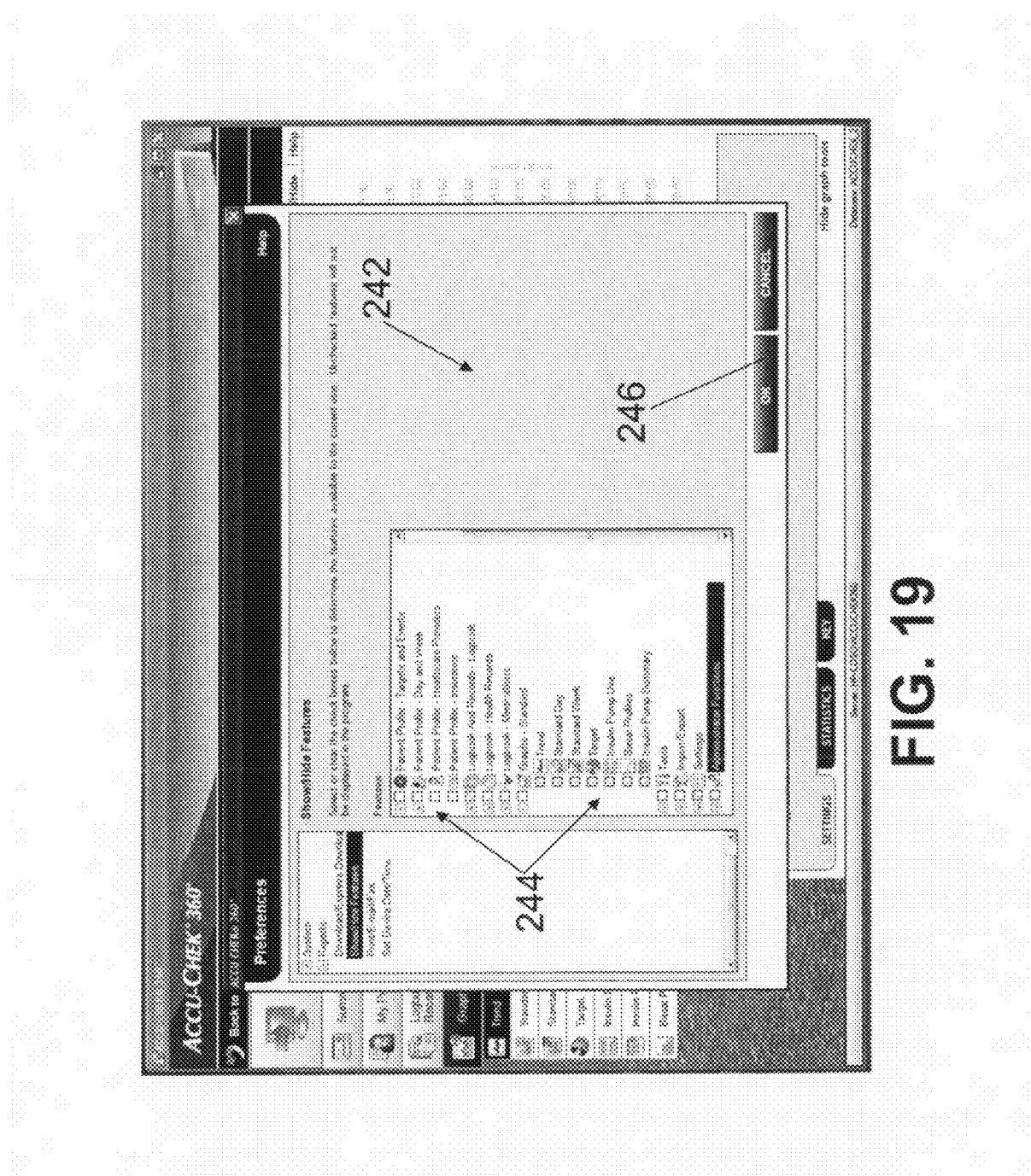
FIG. 19 is an exemplary screen similar to FIG. 18 in which the end user has selected to hide certain features.
Figure 20:
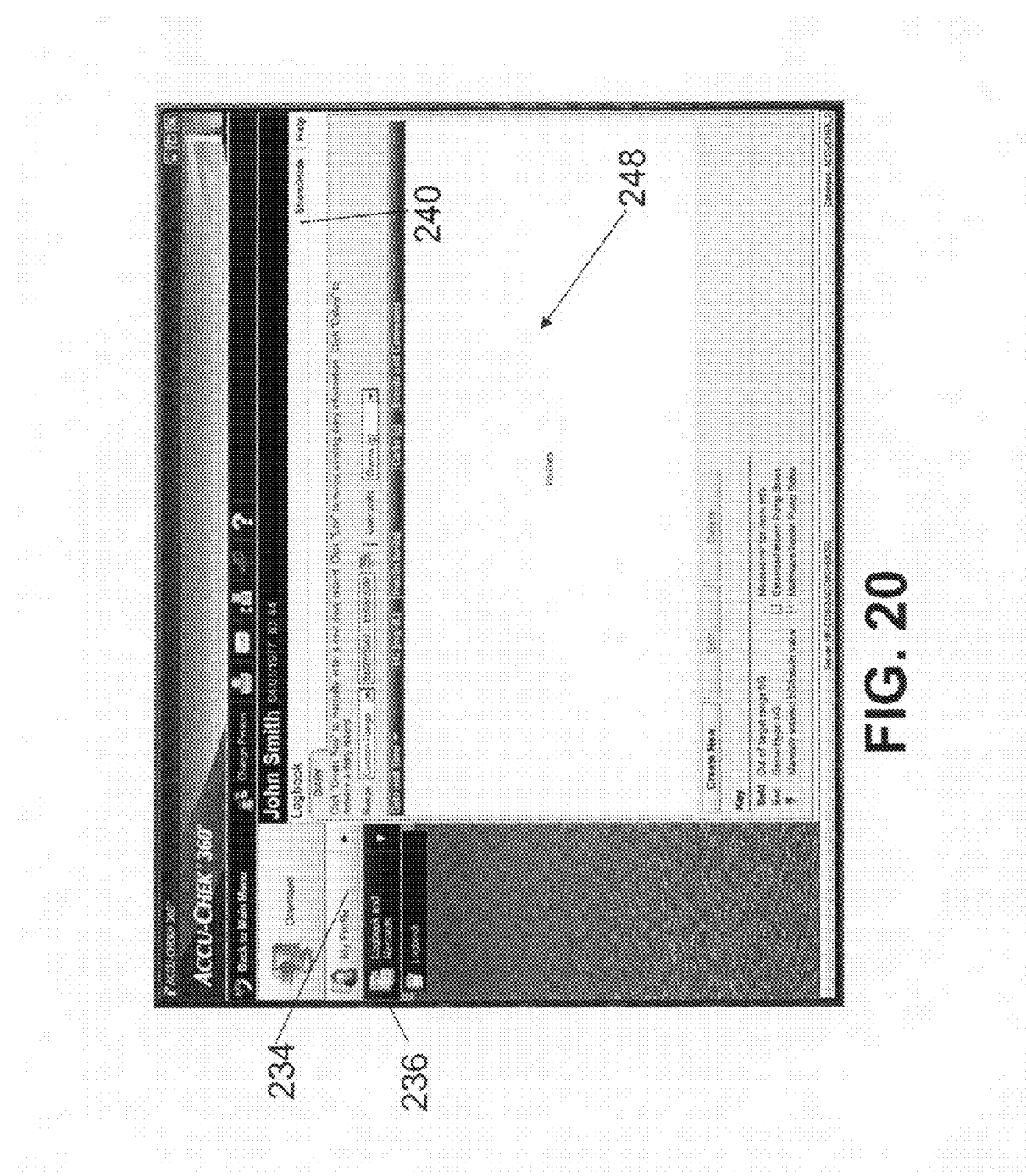
FIG. 20 is an exemplary screen shown on the user interface after certain features and functions were hidden in FIG. 19.

As discussed above with reference to block 174 in FIG. 4, the end user has the ability to "show" and "hide" certain features which were activated and enabled during the steps discussed above. For instance, screen 230 of FIG. 17 is a certain display screen for patient John Smith. Icons 232, 234, 236 and 238 illustrate various enabled and active features and functions of the software application 130 which are available to the end user. The end user can further show or hide certain features by clicking on the "Show/Hide" button 240 in FIG. 17. Clicking on the "Show/Hide" button 240 illustratively displays a "Preferences" screen 242 as illustrated in FIG. 18. The end user can then selectively show or hide certain features displayed when the software program is operated. In the illustrated embodiment, features marked with a check mark in boxes 244 will be displayed in the program while features next to unchecked boxes will not be displayed. For example, if the end user unchecks certain boxes 244 as illustrated in FIG. 19 and then selects the "OK" button 246, the summary and graphs icons 232 and 238 previously shown in FIG. 17 are automatically removed from the display 104 as illustrated in FIG. 20. The features are hidden without requiring the user to shut off the computer 102 or reboot. The user can click on the "Show/Hide" button 240 in FIG. 20 to again display the Preferences screen 242 in FIG. 19 and either check or uncheck certain features. The Preferences screen 242 in FIG. 19 is illustratively the only reference to "hidden" features and functions during operation of the software application 130.

The following Tables I and II illustrate certain features and functions of the diabetes management system. Table I indicates whether disabling of the particular feature or function is permitted by the system administrator as shown in FIG. 16, for example. Table II indicates whether the show/hide feature illustrated in FIGS. 17-20 is allowed for the particular feature or function.

TABLE I

| Primary Feature/Function | Disabling Permitted? |
| --- | --- |
| Devices | No |
| Patient Management | No |
| Tools | Yes |
| Insulin Pump Reports | Yes |
| Settings | No |
| Administrator Functions | Yes |
| Advanced Record Tracking | Yes |
| Advanced Reporting | Yes |
| Population Management | Yes |

TABLE II

| Primary Feature/Function | Hide/Show Allowed? |
| --- | --- |
| Download | No |
| Toolbar | Yes |
| Summary | Yes |
| Patient Profile - Personal | No |
| Patient Profile - Diabetes Therapy | Yes |
| Patient Profile - Targets and Events | Yes |
| Patient Profile - Day and Week | Yes |
| Patient Profile - Healthcare Providers | Yes |
| Patient Profile - Insurance | Yes |
| Logbook and Records - Logbook | No |
| Logbook - Health Records | Yes |
| Logbook - Medications | Yes |
| Logbook - Education | Yes |
| Logbook - Complications | Yes |
| Logbook - Visit Notes | Yes |
| Graphs - Standard | Yes |
| Graphs - Advanced | Yes |
| Graphs - Favorite Reports | Yes |
| Advanced Reports and Letters | Yes |
| Tools | Yes |

TABLE II-continued

| Primary Feature/Function | Hide/Show Allowed? |
|---|---|
| Import/Export | Yes |
| Settings | No |
| Administrator Functions | Yes |

Concepts described herein may be further explained in one of more of the co-filed patent applications entitled HELP UTILITY FUNCTIONALITY AND ARCHITECTURE Ser. No. 11/999,906, METHOD AND SYSTEM FOR GRAPHICALLY INDICATING MULTIPLE DATA VALUES Ser. No. 11/999,853, SYSTEM AND METHOD FOR DATABASE INTEGRITY CHECKING Ser. No. 11/999,856, METHOD AND SYSTEM FOR DATA SOURCE AND MODIFICATION TRACKING Ser. No. 11/999,888, PATIENT-CENTRIC HEALTHCARE INFORMATION MAINTENANCE Ser. No. 11/999,874, EXPORT FILE FORMAT WITH MANIFEST FOR ENHANCED DATA TRANSFER Ser. No. 11/999,867, GRAPHIC ZOOM FUNCTIONALITY FOR A CUSTOM REPORT Ser. No. 11/999,932, (METHOD AND SYSTEM FOR SELECTIVE MERGING OF PATIENT DATA Ser. No. 11/999,859, METHOD AND SYSTEM FOR PERSONAL MEDICAL DATA DATABASE MERGING Ser. No. 11/999,772, METHOD AND SYSTEM FOR WIRELESS DEVICE COMMUNICATION Ser. No. 11/999,879, METHOD AND SYSTEM FOR SETTING TIME BLOCKS Ser. No. 11/999,968, METHOD AND SYSTEM FOR ENHANCED DATA TRANSFER Ser. No. 11/999,911, COMMON EXTENSIBLE DATA EXCHANGE FORMAT Ser. No. 11/999,871, METHOD OF CLONING SERVER INSTALLATION TO A NETWORK CLIENT Ser. No. 11/999,876, METHOD AND SYSTEM FOR QUERYING A DATABASE Ser. No. 11/999,912, METHOD AND SYSTEM FOR EVENT BASED DATA COMPARISON Ser. No. 11/999,921, DYNAMIC COMMUNICATION STACK Ser. No. 11/999,934, SYSTEM AND METHOD FOR REPORTING MEDICAL INFORMATION Ser. No. 11/999,878, METHOD AND SYSTEM FOR MERGING EXTENSIBLE DATA INTO A DATABASE USING GLOBALLY UNIQUE IDENTIFIERS Ser. No. 11/999,947, METHOD AND SYSTEM FOR ACTIVATING FEATURES AND FUNCTIONS OF A CONSOLIDATED SOFTWARE APPLICATION Ser. No. 11/999,880, METHOD AND SYSTEM FOR DATA SELECTION AND DISPLAY Ser. No. 11/999,896, METHOD AND SYSTEM FOR ASSOCIATING DATABASE CONTENT FOR SECURITY ENHANCEMENT Ser. No. 11/999,951, HEALTHCARE MANAGEMENT SYSTEM HAVING IMPROVED PRINTING OF DISPLAY SCREEN INFORMATION Ser. No. 11/999,855, METHOD AND SYSTEM FOR CREATING REPORTS Ser. No. 11/999,851, METHOD AND SYSTEM FOR CREATING USER-DEFINED OUTPUTS Ser. No. 11/999,905, DATA DRIVEN COMMUNICATION PROTOCOL GRAMMAR Ser. No. 11/999,770, and METHOD AND SYSTEM FOR MULTI-DEVICE COMMUNICATION Ser. No. 11/999,866, the entire disclosures of which are hereby expressly incorporated herein by reference.

It should be understood that the concepts described herein may relate to diabetes management software systems for tracking and analyzing health data, such as, for example, the ACCU-CHEK® 360° product provided by Roche Diagnostics. However, the concepts described herein may also have applicability to apparatuses, methods, systems, and software in fields that are unrelated to healthcare. Furthermore, it should be understood that references in this patent application to devices, meters, monitors, pumps, or related terms are intended to encompass any currently existing or later developed apparatus that includes some or all of the features attributed to the referred to apparatus, including but not limited to the ACCU-CHEK® Active, ACCU-CHEK® Aviva, ACCU-CHEK® Compact, ACCU-CHEK® Compact Plus, ACCU-CHEK® Integra, ACCU-CHEK® Go, ACCU-CHEK® Performa, ACCU-CHEK® Spirit, ACCU-CHEK® D-Tron Plus, and ACCU-CHEK® Voicemate Plus, all provided by Roche Diagnostics or divisions thereof.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

The invention claimed is:

1. A method of customizing a consolidated software application including a plurality of features and functions for a particular end user, the method comprising:
providing an activation key for use during installation of the consolidated software application wherein the activation key is created by a marketing group;
activating selected features and functions of the consolidated software application with the activation key during installation of the consolidated software application on a computing device having a user interface accessible by an end user;
displaying the activated features and functions of the consolidated software application which were activated during the activating step on the user interface accessible by a system administrator;
receiving at least one input to permit the system administrator to selectively enable and disable access for the end user to the activated features and functions of the consolidated software application after installation of the consolidated software application on the computing device;
displaying the activated and enabled features and functions of the consolidated software application on the user interface accessible to the end user, and wherein information related to non-active features and functions of the consolidated software application with the activation key which were not activated by the marketing group during the activating step is not displayed on the user interface accessible by the system administrator and the end user;
receiving at least one input to permit the end user to selectively show and hide the activated and enabled features and functions of the consolidated software application from display on the user interface; and
removing the activated and enabled features and functions of the consolidated software application that the end user selects to hide from display on the user interface accessible to the end user.

2. The method of claim 1, wherein the information related to disabled features and functions that were disabled by the system administrator during the selectively enabling and disabling activated features step is also not displayed on the user interface accessible by the end user.

3. The method of claim 1, wherein the activation key identifies a product class of the consolidated software application selected from a consumer mode and a healthcare professional mode.

4. The method of claim 1, wherein the activation key establishes a trial mode of operation for the consolidated software application on a computing device, the activation key indicating a number of days that the end user is allowed to operate the consolidated software application in the trial mode.

5. The method of claim 1, wherein the activation key indicates included countries for which the activation key is valid.

6. The method of claim 5, wherein the activation key also indicates excluded countries for which the activation key is invalid.

7. The method of claim 1, wherein the activation key includes a plurality of hexadecimal characters to indicate which features and functions of the consolidated software application are activated.

8. The method of claim 1, wherein the activating step further comprises allowing an installer of the consolidated software application to selectively activate features and functions during installation separate from those features and functions activated by the activation key.

9. The method of claim 1, wherein the consolidated software application is configured to provide a plurality of different features and functions to process physiological information data received from a portable device related to management of a health condition, the consolidated software application including instructions to display representations of physiological information data on the user interface.

10. The method of claim 1, wherein the activating step is based at least in part on a geographic region of the end user.

11. The method of claim 1, wherein the activating step is based at least in part on a type of end user.

12. The method of claim 11, wherein the end user is one of a consumer, a healthcare professional, a managed care provider, a health maintenance organization, and a payor.

13. The method of claim 1, wherein the activating step is based at least in part on an authorized field of use of the end user.

14. The method of claim 1, wherein the consolidated software application includes a base application including the plurality of base feature sets which are always activated and enabled, and a plurality of additional feature sets which may be selectively activated during the activating step and selectively enabled and disabled during the step of receiving at least one input to permit the system administrator to selectively enable and disable activated features.

15. The method of claim 1, wherein the activating step establishes a language for use on the user interface accessible by an end user.

16. The method of claim 1, wherein the activating step establishes at least one language for reports generated by the consolidated software application.

17. The method of claim 1, wherein the consolidated software application includes a plurality of styles of display icons, graphics, and color schemes which may be used on a display of the user interface accessible by the end user, and wherein the activating step activates selected styles of icons, graphics, and color schemes to adjust a look and feel of the software.

18. The method of claim 1, wherein the activating step selects a background image for use on a display of the user interface accessible by the end user from a plurality of background images in the consolidated software application.

19. The method of claim 1, wherein the activating step selects different messages, instructions, and help topics for use on a display of the user interface accessible by the end user based on the activated and enabled features and functions.

20. The method of claim 1, wherein the features and functions include hardware connectivity software used to permit the computing device to communicate with a plurality of external devices, and wherein the activating step selectively activates portions of the hardware connectivity software for an identified external device.

21. The method of claim 20, wherein the external device is one of a glucose meter, an infusion pump, a cellular phone, and a personal data assistants (PDA).

22. A computing device configured to customize a consolidated software application including a plurality of features and functions for a particular end user, comprising:
a memory having computer executable instructions, and when the computer executable instructions are executed, the computer device is configured to:
provide an activation key for use during installation of the consolidated software application wherein the activation key is created by a marketing group;
activate selected features and functions of the consolidated software application with the activation key during installation of the consolidated software application on the computing device having a user interface accessible by an end user;
display the activated features and functions of the consolidated software application which were activated during the activating step on the user interface accessible by a system administrator;
receive at least one input to permit the system administrator to selectively enable and disable access for the end user to the activated features and functions after installation of the consolidated software application on the computing device;
display the activated and enabled features and functions of the consolidated software application on the user interface accessible to the end user, and wherein information related to non-active features and functions of the consolidated software application with the activation key which were not activated by the marketing group during the activating step is not displayed on the user interface accessible by the system administrator and the end user;
receive at least one input to permit the end user to selectively show and hide the activated and enabled features and functions of the consolidated software application from display on the user interface; and
remove the activated and enabled features and functions of the consolidated software application that the end user selects to hide from display on the user interface accessible to the end user.

23. A method of multi-level customization of a consolidated software application by a marketing group, a system administrator, and an end user, the method comprising:
receiving at least one input to permit the marketing group to:
selectively activate features and functions of the consolidated software application with an activation key based on at least one of a geographic region of the end user, a type of the end user, and permitted field of use of the end user during installation of the consolidated software application on a computing device having a user interface accessible by the end user;
wherein the consolidated software application is configured to provide a plurality of different features and functions to process physiological information data; and
wherein information related to non-active features and functions of the consolidated software application with the activation key which were not activated by the marketing group is not displayed on user interfaces accessible by the system administrator and the end user;

receiving at least one input to permit the system administrator to selectively enable and disable access for the end user to the activated features and functions of the consolidated software application after installation of the consolidated software application;

receiving at least one input to permit the end user to selectively show and hide the activated and enabled features and functions of the consolidated software application from display on the user interface; and removing the activated and enabled features and functions of the consolidated software application that the end user selects to hide from a display of the user interface accessible to the end user.

24. The method of claim 23, wherein information related to disabled features and functions that were disabled by the system administrator is also not displayed on the user interface accessible by the end user.

25. The method of claim 23, wherein the step of receiving at least one input to permit a marketing group to selectively activate the features and functions of the consolidated software application includes providing an activation key for use during installation of the consolidated software application.

26. The method of claim 25, wherein the step of receiving at least one input to permit a marketing group to selectively activate the features and functions of the consolidated software application further comprises allowing an installer of the consolidated software application to selectively activate features and functions during installation separate from those features and functions activated by the activation key.

27. The method of claim 23, wherein the consolidated software application is configured to provide a plurality of different features and functions to process physiological information data received from a portable device related to management of a health condition, the consolidated software application including instructions to display representations of physiological information data on the user interface.

28. The method of claim 23, wherein the consolidated software application includes a plurality of styles of display icons, graphics, and color schemes which may be used on a display of the user interface accessible by the end user, the marketing group activating selected styles of icons, graphics, and color schemes to adjust a look and feel of the software.

29. The method of claim 23, wherein the marketing group selectively activates a background image for use on a display of the user interface accessible by the end user from a plurality of background images in the consolidated software application.

30. The method of claim 23, wherein the features and functions of the consolidated software application include a plurality of different messages, instructions, and help topics for use on a display of the user interface accessible by the end user based on the activated and enabled features and functions.

31. The method of claim 23, wherein the features and functions of the consolidated software application include hardware connectivity software used to permit the computing device to communicate with a plurality of external devices, at least one of the marketing group and the system administrator selectively activating portions of the hardware connectivity software for an identified external device.

32. A computing device configured for multi-level customization of a consolidated software application by a marketing group, a system administrator, and an end user, comprising:

a memory having computer executable instructions, and when the computer executable instructions are executed, the computing device is configured to:

receive at least one input to permit the marketing group to:

selectively activate features and functions of the consolidated software application with an activation key based on at least one of a geographic region of the end user, a type of the end user, and permitted field of use of the end user during installation of the consolidated software application on a computing device having a user interface accessible by the end user;

wherein the consolidated software application is configured to provide a plurality of different features and functions to process physiological information data; and wherein information related to non-active features and functions of the consolidated software application with the activation key which were not activated by the marketing group is not displayed on user interfaces accessible by the system administrator and the end user;

receive at least one input to permit the system administrator to selectively enable and disable access for the end user to the activated features and functions of the consolidated software application after installation of the consolidated software application;

receive at least one input to permit the end user to selectively show and hide the activated and enabled features and functions of the consolidated software application from display on the user interface; and remove the activated and enabled features and functions of the consolidated software application that the end user selects to hide from a display of the user interface accessible to the end user.

33. A healthcare management system configured to receive and process physiological information data related to at least one patient from a portable device, the healthcare management system comprising:

a computing device configured to access and download physiological information data from a portable device;

a memory accessible by the computing device to store the downloaded physiological information data;

at least one user interface having a display which receives display information from the computing device;

software configured to operate on the computing device and implement a plurality of different features and functions to manage the physiological information data from the portable device related to management of a health condition, the software including instructions to display representations of physiological information data included in the memory on the display of the user interface; and the software further comprises:

providing an activation key for use during installation of the consolidated software application wherein the activation key is created by a marketing group;

activating selected features and functions of the consolidated software application during installation of the consolidated software application;

identifying a product class of the consolidated software application and selecting from a consumer mode and a healthcare professional mode;

displaying the activated features and functions of the consolidated software application to a system administrator;

removing non-activated features and functions of the consolidated software application from a view of the system administrator;

permitting the system administrator to selectively enable and disable end user access to the activated features and functions of the consolidated software application after installation of the consolidated software application;

displaying the activated and enabled features and functions of the consolidated software application to the end user;

removing the non-enabled, activated features and functions of the consolidated software application from a view of the end user;

permitting the end user to selectively show and hide the activated and enabled features and functions of the consolidated software application from the view of the end user;

displaying information related to the shown activated and enabled features and functions selected by the end user; and removing the activated and enabled features and functions of the consolidated software application which were hidden by the end user from the view of the end user.

* * * * *